(12) United States Patent
Oishi

(10) Patent No.: US 10,570,483 B2
(45) Date of Patent: Feb. 25, 2020

(54) COPPER-BASED ALLOY CASTING IN WHICH GRAINS ARE REFINED

(71) Applicant: Mitsubishi Shindoh Co, Ltd., Tokyo (JP)

(72) Inventor: Keiichiro Oishi, Osaka (JP)

(73) Assignee: Mitsubishi Shindoh Co., Ltd., Tokyo (JP)

( * ) Notice: Subject to any disclaimer, the term of this patent is extended or adjusted under 35 U.S.C. 154(b) by 13 days.

(21) Appl. No.: 16/033,689

(22) Filed: Jul. 12, 2018

(65) Prior Publication Data

US 2019/0040498 A1 Feb. 7, 2019

Related U.S. Application Data

(63) Continuation of application No. 10/596,849, filed as application No. PCT/JP2005/008662 on May 2, 2005, now abandoned.

(30) Foreign Application Priority Data

Aug. 10, 2004 (JP) .................. 2004-233952

(51) Int. Cl.
*C22C 9/04* (2006.01)
*B22D 21/02* (2006.01)
(Continued)

(52) U.S. Cl.
CPC .............. *C22C 9/04* (2013.01); *B22D 21/022* (2013.01); *B22D 21/025* (2013.01); *B22D 27/00* (2013.01);
(Continued)

(58) Field of Classification Search
CPC ..... C22F 1/08; C22C 9/00; C22C 9/04; C22C 1/03; B22D 21/0022; B22D 21/0025; B22D 27/00
See application file for complete search history.

(56) References Cited

U.S. PATENT DOCUMENTS 2,521,663 A 9/1950 Zunick
3,676,083 A 7/1972 Cheney et al.
(Continued)

FOREIGN PATENT DOCUMENTS

EP 1 681 360 A1 7/2006
JP 49-40226 4/1974
(Continued)

OTHER PUBLICATIONS

Gubner, Rolf et al., Grain Boundary Corrosion of Copper Canister Weld Material, TR-06-01 (Svensk Kärnbränslehantering AB 2006).
(Continued)

*Primary Examiner* — C Melissa Koslow
(74) *Attorney, Agent, or Firm* — Merchant & Gould, P.C.

(57) ABSTRACT

A copper-based alloy casting includes 69 to 88% of Cu, 2 to 5% of Si, 0.0005 to 0.04% of Zr, 0.01 to 0.25% of P by mass, and a remainder including Zn and inevitable impurities, and satisfies 60≤Cu−3.5×Si−3×P≤71. Further, mean grain size after melt-solidification is 100 μm or less, and α, κ and γ-phases occupy more than 80% of phase structure. Furthermore, the copper-based alloy casting according to the invention can further include at least one element selected from a group consisting of 0.001 to 0.2% of Mg, 0.003 to 0.1% of B, 0.0002 to 0.01% of C, 0.001 to 0.2% of Ti and 0.01 to 0.3% of rare earth element.

7 Claims, 9 Drawing Sheets

(51) Int. Cl.
| | |
|---|---|
| *C22C 1/06* | (2006.01) |
| *C22C 30/02* | (2006.01) |
| *C22C 30/06* | (2006.01) |
| *C22F 1/08* | (2006.01) |
| *B22D 27/00* | (2006.01) |
| *C22C 1/03* | (2006.01) |
| *C22C 9/00* | (2006.01) |

(52) U.S. Cl.
CPC .................. *C22C 1/03* (2013.01); *C22C 1/06* (2013.01); *C22C 9/00* (2013.01); *C22C 30/02* (2013.01); *C22C 30/06* (2013.01); *C22F 1/08* (2013.01)

(56) References Cited

U.S. PATENT DOCUMENTS

| | | | |
|---|---|---|---|
| 3,912,552 | A | 10/1975 | Schultz et al. |
| 3,928,028 | A | 12/1975 | Yarwood |
| 4,047,978 | A | 9/1977 | Parikh et al. |
| 4,055,445 | A | 10/1977 | Pops |
| 4,110,132 | A * | 8/1978 | Parikh ........................ C22F 1/08 148/432 |
| 4,238,249 | A | 12/1980 | Ruchel |
| 4,353,415 | A | 10/1982 | Klaschka et al. |
| 4,708,739 | A | 11/1987 | Kellie et al. |
| 4,710,349 | A | 12/1987 | Yamazaki et al. |
| 4,786,469 | A | 11/1988 | Weber et al. |
| 4,822,560 | A | 4/1989 | Oyama et al. |
| 4,826,736 | A | 5/1989 | Nakamura et al. |
| 5,370,840 | A | 12/1994 | Caron et al. |
| 5,565,045 | A | 10/1996 | Caron et al. |
| 5,871,861 | A | 2/1999 | Hirokou et al. |
| 6,401,323 | B1 | 6/2002 | Roller et al. |
| 6,413,330 | B1 | 7/2002 | Oishi |
| 6,627,011 | B2 | 9/2003 | Sugawara et al. |
| 7,909,946 | B2 * | 3/2011 | Oishi .................. B22D 21/025 148/434 |
| 2002/0006351 | A1 | 1/2002 | Sugawara et al. |
| 2004/0234412 | A1 | 11/2004 | Oishi et al. |
| 2005/0039827 | A1 | 2/2005 | Yamagishi et al. |
| 2006/0222557 | A1 | 10/2006 | Pike, Jr. |
| 2008/0073005 | A1 | 3/2008 | Buck |
| 2010/0297464 | A1 | 11/2010 | Oishi |

FOREIGN PATENT DOCUMENTS

| | | |
|---|---|---|
| JP | 52-107227 | 9/1977 |
| JP | 54-92516 A | 7/1979 |
| JP | 55-070494 A | 5/1980 |
| JP | 61-000542 | 1/1986 |
| JP | 61048547 | 3/1986 |
| JP | 61133357 A | 6/1986 |
| JP | 62-274036 | 11/1987 |
| JP | 62-297429 | 12/1987 |
| JP | 1-162737 | 6/1989 |
| JP | 02-170954 A | 7/1990 |
| JP | 3-291344 | 12/1991 |
| JP | 04-224645 A | 8/1992 |
| JP | 6-058688 A | 3/1994 |
| JP | 6-184669 A | 7/1994 |
| JP | 06-184674 A | 7/1994 |
| JP | 10-046270 A | 2/1998 |
| JP | 10-152735 | 6/1998 |
| JP | 11-001736 A | 1/1999 |
| JP | 2000-119775 A | 4/2000 |
| JP | 2000-199023 A | 7/2000 |
| JP | 2001-247923 | 9/2001 |
| JP | 2001-247923 A | 9/2001 |
| JP | 2002-030364 A | 1/2002 |
| JP | 2004-100041 A | 4/2004 |
| JP | 2004-100042 A | 4/2004 |
| JP | 2004-143541 | 5/2004 |
| JP | 2004-183056 A | 7/2004 |
| JP | 2004-233952 A | 8/2004 |
| WO | 94/10352 | 5/1994 |
| WO | 2004/022805 A1 | 3/2004 |

OTHER PUBLICATIONS

ASM Specialty Handbook: Copper and Copper Alloys, pp. 1-9 (ASM International 2001).
Procedures: Copper Welding, at http://www.brazing.com/techguide/procedures/copper_welding.asp (downloaded Jun. 13, 2012, six pages.
Metals Handbook® Ninth Edition, vol. 9, Metallography and Microstructures 155 and 408 (American Society for Metals 1985).
Metals Handbook 8th Ed., vol. 7, Atlas of Microstructures of Industrial Alloys 280 (American Society for Metals 1972).
ASM Specialty Handbook® Copper and Copper Alloys 243-246 (2001).
Materials Mechanical Size Effects: a Review, 23 Materials Technology 193-209 (2008).
Metals Handbook, 8th Edition, 1973, p. 169, "Solidification Structures of Copper Alloy Ingots."
ASM Specialty Handbook, Copper and Copper Alloys, 2001, pp. 242-247, "Heat Treating."
Metals Handbook, vol. 9, Metallography and Microstructures, 1985, pp. 2, 5, 8, 9 and 15.
ASM Specialty Handbook, Copper and Copper Alloys, 2001, pp. 213-215, "Forging and Extrusion."
International Search Report issued in corresponding application PCT/JP2005/008662, completed Jul. 21, 2005 dated Aug. 9, 2005.
Petch, N.J., The Cleavage Strength of Polycrystals, Journal of the Iron and Steel Institute, May 1953, pp. 25-28.
Hall, E.O., The Deformation and Ageing of Mild Steel, Mar. 1951, pp. 747-753.
R. Mannheim, Untersuchung der Kornfienung von Kupfer-Zinn-Legierungen mit Zirconium und/oder Bor und Eisen sowie ihres Einflusses auf die mechanischen Eigenschaften, Giessereiforschung 40 1998 Nr. 1, pp. 1-16.
O. Bustos, Estudio de la combinanción de los procesos de afinamiento de grano de colada y filtrado en latones, Rev. Metal. Madrid, 35 (4), 1999, pp. 222-232.
M. Sadayappan, Fading of Grain Refinement in Leaded Yellow Brass (C85800) and SeBiLOY III (C89550, EnviroBrass III), AFS Transactions 01-116, 2001 American Foundry Society, pp. 705-713.
D. Cousineau, Grain Refinement of Permanent Mold Cast Copper-Base Alloys, AFS Transactions 02-108, 2002 American Foundry Society, pp. 505-514.
J.P. Thomson, Evaluation of Grain Rfinement of Leaded Yellow Brass (C85800) and EnviroBrass III (C89550) using Thermal Analysis, AFS Transactions 2003, pp. 417-434.
F.A. Fasoyinu, Effects of Grain Refinement on Hot Tear Resistance and Shrinkage Characteristics of Permanent Mold Cast Yellow Brass (C85800), pp. 327-337.
M. Sadayappan, Fading of Grain Refinement in Permanent Mold Cast Copper Alloys, AFS Transactions 2004 © American Foundry Society, Des Plaines IL USA, pp. 521-526.
Prof. Dr.-Ing. W. Reif, A New Grain Refiner for Copper-Zinc Alloys containing 25-42%Zinc, Metall 41. Jahrgang Heft Nov. 11, 1987, pp. 1131-1137.
M. Sadayappan, GrainRefinement of Copper Base Alloys, vol. 1—Plenary Lectures/Movement of Copper and Industry Outlook/Copper Applications and Fabrication, 1999, pp. 279-291.
M. Sadayappan, Grain Refinement of Permanent Mold Cast Silicon Brass, Silicon Bronze and Red Brass, AFS Transactions, pp. 337-342.
A. Couture, Grain Refinement of Sand Cast Bronzes and its Influence on Their Properties, AFS Cast Metals Research Journal, Mar. 1974, pp. 1-5.
M. Sadayappan, Grain Refinement Studies on Leaded and Bi/Se Modified Yellow Brasses, pp. 45-58.
M. Sahoo, An Overview of ICA-Funded Research and Development at MTL/Canmet, pp. 1-12.

(56) References Cited

OTHER PUBLICATIONS

Metal Handbook Ninth Edition, vol. 9, Metallography and Microstructures, pp. 629-631.
Metals Handbook Ninth Edition, vol. 9, Metallography and Microstructures (American Society for Metals), pp. 641-642.
pp. 290 & C-2 of Metals Handbook 8th Edition, vol. 7, Atlas of Microstructures of Industrial Alloys (American Society for Metals).
p. 286 of Metals Handbook 8th Edition, vol. 7, Atlas of Microstructures of Industrial Alloys (American Society for Metals).
International Search Report issued in related application PCT/JP2205/018107, completed Dec. 13, 2005 dated Dec. 20, 2005.
International Search Report issued in related application PCT/JP2005/014698, completed Sep. 2, 2005 dated Sep. 20, 2005.
International Search Report issued in related application PCT/JP2005/014697, completed Sep. 2, 2005 dated Sep. 20, 2005.
Binary Alloy Phase Diagrams, vol. 1, American Society for Metals, pp. 819-820, 971.
Cast Nonferous: Heat Treating of Copper and Copper Alloys, downloaded Nov. 2, 2010, from http://www.keytometals.com/Article25.htm, two pages.
Visual Acuity of the Human Eye, 3 pages, downloaded from http://www.ndt.ed.org/EductationResources/CommunityCollege/PenetrantTest/Introduction/visualacuity.htm, Sep. 17, 2004.
V. Ryan, Annealing Metals, downloaded Nov. 2, 2010 from http://www.technologystudent.com/equip1/heat3.htm, 2 pages.
p. 301 of Metals Handbook 8th Edition, vol. 8, Metallography, Structures and Phase Diagrams,1973.
Annual Book of ASTM Standards 2000, vol. 02.01, Section 2, p. 876.
p. 171 of Metals Handbook 8th Edition, vol. 8, Metallography, Structures and Phase Diagrams,1973.
pp. 641, 642 and 411 of Metals Handbook® Ninth Edition, vol. 9, Metallography and Microstructures, 1985.
pp. 1, 3, 5, 15 and 16 of Terms and Definition of Metals Handbook 9th Edition, vol. 9, Metallography and Microstructures, American Society for Metals.
pp. 257-259 os ASM Specialty Handbook, Copper and Copper Alloys, ASM.
pp. 9 and 15 of Terms and Definition of Metals Handbook 9th Edition, vol. 9, Metallography and Microstructures, American Society for Metals.
E. Paul Degarmo, Materials and Processes in Manufacturing 276-295 (John Wiley & Sons, Inc. 9th Ed. 2003), filed in a related application as Exhibit A1.
"Casting and Solidification Process," dated Jan. 9, 2010, at http://classes.engr.oregonstate.edu/mime/winter2010/ie337-001/Laboratories/5.Solidification%20Lab.pdf, downloaded Nov. 23, 2011, three pages, filed in a related application as Exhibit B1.

\* cited by examiner

No.9

No.103

No.9  (15 μm)

No.10  (30 μm)

No.6  (85 μm)

No.112 (150 μm)

No.110 (500 μm)

No.103 (800 μm)

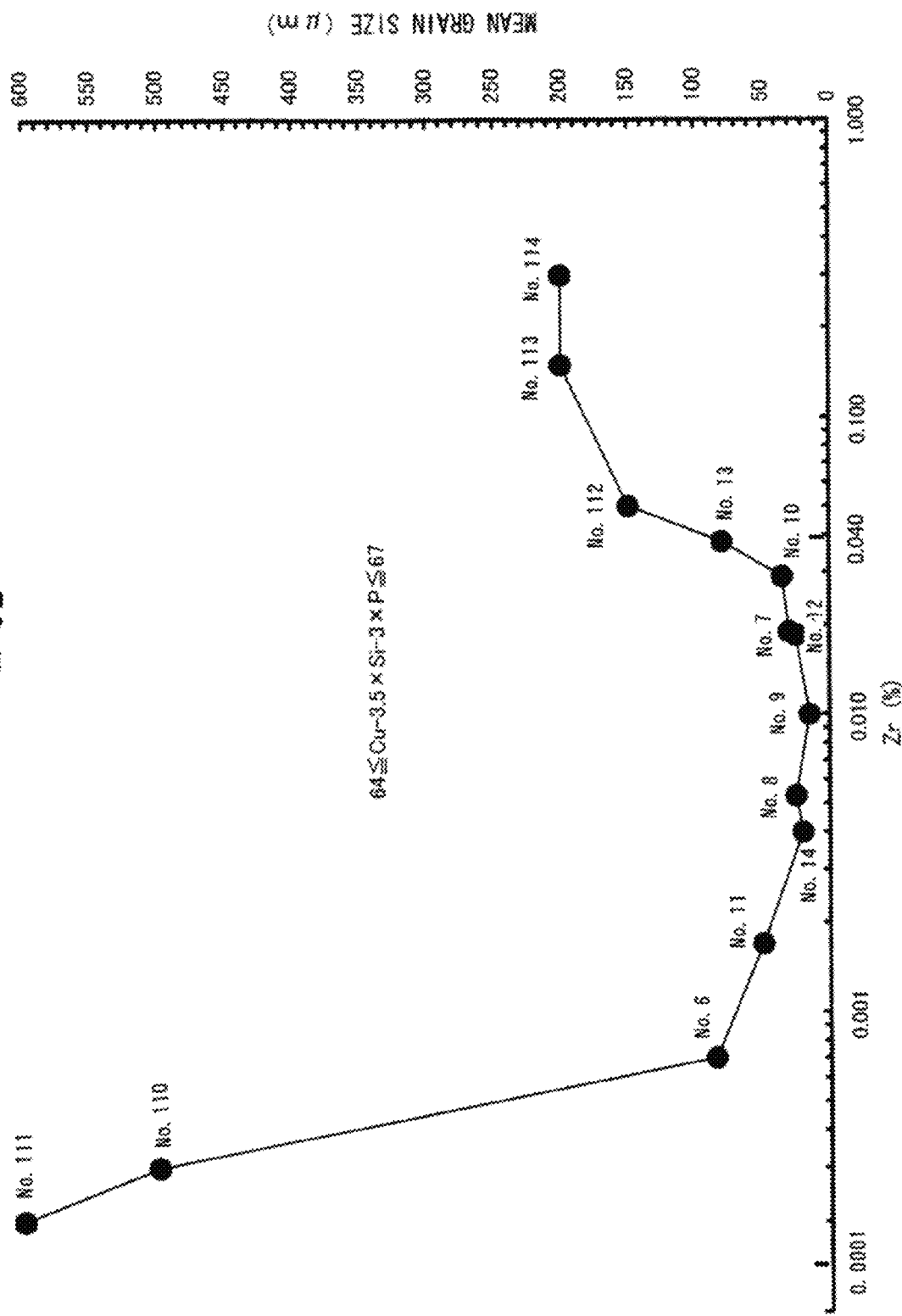

(25 μm)

No.8

(350 μm)

No.115

(500 μm)

No.110

×3.5

COPPER-BASED ALLOY CASTING IN WHICH GRAINS ARE REFINED

This application is a Continuation Application of U.S. patent application Ser. No. 10/596,849, Nov. 27, 2006, which is a National Phase Application in the United States of International Patent Application No. PCT/JP2005/008662 filed May 2, 2005, which claims priority on Japanese Patent Application No. 2004-233952, filed Aug. 10, 2004. The entire disclosures of the above patent applications are hereby incorporated by reference.

BACKGROUND OF THE INVENTION

1. Technical Field

The present invention relates to a copper-based alloy casting in which grains are refined after melt-solidification, and particularly, to a Cu—Zn—Si alloy casting.

2. Related Art

It is well known that, like a common metallic material, the proof stress of a copper-based alloy is improved by grain refinement, and it is told that the strength of the copper-based alloy is inversely proportional to the square root of the grain size on the basis of the Hall-Petch theory.

Basically, the grains of the copper-based alloy are refined as follows: (A) grains are being refined during the melt-solidification of the copper-based alloy, or (B) grains are refined by performing deformation process such as rolling or heat treatment on the melt-solidified copper alloy (ingot such as slurry or the like; casting such as diecast or the like; and hot forged parts or the like), in which stacking energy such as distortion energy or the like acts as a driving force.

Zr is a well-known element contributing to the grain refinement in both (A) and (B) cases.

However, in (A) case, the effect of Zr on the grain refinement during the melt-solidification is considerably influenced by the other components and the amount thereof, whereby a desired level of grain refinement cannot be achieved.

As a result, grains are, in general, refined like (B) case, that is, heat treatment is performed on a melt-solidified ingot, casting or the like, and then the alloy is distorted for grain refinement.

These are disclosed in JP-B-38-20467 and JP-A-2004-100041.

In JP-B-38-20467, solution heat treatment and 75% cold-working are performed on a copper alloy containing Zr, P and Ni in order to examine the mean grain size. The publication illustrates that the grain size decreases as the amount of Zr increases by showing that the mean grain sizes are 280 μm (no Zr contained), 170 μm (0.05% of Zr contained), 50 μm (0.13% of Zr contained), 29 μm (0.22% of Zr contained) and 6 μm (0.89% of Zr contained) respectively. In addition, the publication suggests that the optimum amount of Zr is 0.05 to 0.3%, considering adverse effects induced when Zr is contained excessively.

JP A 2004-100042 discloses that, in a copper alloy containing 0.15 to 0.5% of Zr, grains can be reduced to about 20 μm or less in the mean grain size by performing solution heat treatment and deformation process, which is to add distortion to the alloy.

However, performing the above treatment and process after casting for the purpose of grain refinement, like (B) case, causes cost to increase, and sometimes it is impossible to perform deformation process for distortion-adding due to the shapes of casting parts.

Therefore, it is preferable that grains are being refined during the melt-solidification of the copper-based alloy like (A) case.

However, as described above, in (A) case, since the effect of Zr on the grain refinement during the melt-solidification is considerably influenced by the other elements and the amount thereof, the grain refinement is not necessarily promoted by the increase of Zr amount. In addition, the affinity of Zr to oxygen is so high that Zr is susceptible to oxidation when dissolved and added in the air, whereby the process yield is very low. As a result, a considerable amount of raw material must be injected during pouring even when a casting contains a small amount of Zr.

Meanwhile, if too many oxides are generated during dissolving, the oxides can enter the mold during pouring, and thus casting defects occur. In order to prevent the oxides from being generated, it can be a good method to dissolve and cast the alloy in vacuum or inert gas atmosphere, however, it leads to cost rise.

Furthermore, Zr is an expensive element. Therefore it is preferable, from an economic viewpoint, to contain a small amount of Zr.

As a result, a copper-based alloy casting, the amount of Zr of which is reduced as much as possible, and the grains of which are refined after melt-solidification, is required.

In a Cu—Zn—Si alloy, Si improves the mechanical properties or the like. However, due to Si, cracks and cavities easily occur during the melt-solidification, whereby shrinkage cavities become large, and casting defects such as shrinkage cavity or the like easily occur. The above phenomena are mainly induced by the following facts: as the amount of Si increases, the solidification temperature range between liquidus temperature and solidus temperature is widened, and the thermal conductivity decreases. Furthermore, it can be found out from the solidified structure of Cu—Zn—Si alloy in the related art that dendrites are shaped, and the arms of the dendrites hinder the removal of porosities generated in the casting. Therefore, the shrinkage cavities remain in the casting, and large shrinkage cavities are generated locally.

The present inventor found out that, if the grains are being refined during the melt-solidification, shrinkage stress generated at the final stage of solidification decreases, and stresses exerting solid phases are dispersed. Therefore, cracks and cavities seldom occur, and the arms of the dendrites are cut. In addition, porosities are easily removed, and shrinkage cavities are smoothly generated. As a result, a casting without casting defect can be obtained.

SUMMARY

It is an object of an aspect of the invention to provide a copper-based alloy in which grains are being refined during the melt-solidification, and more specifically, to provide a Cu—Zn—Si alloy casting in which grains are refined to be 100 μm or less in the mean grain size after melt-solidification.

In order to solve the above problems, a first copper-based alloy casting according to the invention includes 69 to 88% of Cu, 2 to 5% of Si, 0.0005 to 0.04% of Zr, 0.01 to 0.25% of P by mass, and a remainder includes Zn and inevitable impurities, and satisfies $60 \leq Cu - 3.5 \times Si - 3 \times P \leq 71$. Further, mean grain size after melt-solidification is 100 μm or less, and α, κ and γ-phases occupy more than 80% of phase structure.

A second copper-based alloy casting according to the invention further includes, in addition to the composition of the first copper-based alloy casting, at least one element selected from a group consisting of 0.001 to 0.2% of Mg, 0.003 to 0.1% of B, 0.0002 to 0.01% of C, 0.001 to 0.2% of Ti and 0.01 to 0.3% of rare earth element as a grain-refining element, and satisfies 60≤Cu−3.5×Si−3×P−0.5×[i]+0.5×[ii]≤71. Here, [i] is a group consisting of Mg and B, and [ii] is a group consisting of C, Ti and rare earth element.

A third copper-based alloy casting according to the invention further includes, in addition to the composition of the first copper-based alloy casting, at least one element selected from a group consisting of 0.02 to 1.5% of Al, 0.2 to 4.0% of Mn and 0.01 to 0.2% of Cr as a strength and wear resistance-improving element, and satisfies 60≤Cu−3.5×Si−3×P−1.8×Al+a×Mn+0.5×Cr≤71 (a=2 in a case that Mn is contained more than 0.5% and satisfies 0.2×Si≤Mn≤2.0×Si, and a=0.5 in the other cases).

A fourth copper-based alloy casting according to the invention further includes, in addition to the composition of the second copper-based alloy casting, at least one element selected from a group consisting of 0.02 to 1.5% of Al, 0.2 to 4.0% of Mn and 0.01 to 0.2% of Cr as a strength and wear resistance-improving element, and satisfies 60≤Cu−3.5×Si−3×P−0.5×[i]+0.5×[ii]−1.8×Al+a×Mn+0.5×Cr≤71 (a=2 in a case that Mn is contained more than 0.5% and satisfies 0.2×Si≤Mn≤2.0×Si, and a=0.5 in the other cases).

First to fourth copper-based alloy castings according to the invention can further include at least one element selected from a group consisting of 0.1 to 2.5% of Sn, 0.02 to 0.25% of Sb and 0.02 to 0.25% of As as a corrosion resistance-improving element, and at least one element selected from a group consisting of 0.004 to 0.45% of Pb, 0.004 to 0.45% of Bi, 0.03 to 0.45% of Se and 0.01 to 0.45% of Te as a machinability-improving element.

In this specification, 'mean grain size after melt-solidification' means the mean grain size measured after melt-solidification of the copper-based alloys of predetermined compositions, on which no deformation process such as rolling and heat treatment are performed.

BRIEF DESCRIPTION OF THE DRAWINGS

FIG. 9B is a graph of FIG. 9A, wherein the amount of Zr is expressed in logarithmic scale;

FIG. 13A is a view of final solidification portion evaluated 'good', FIG. 13C is a view of final solidification portion evaluated 'bad', and FIG. 13B is a view of final solidification portion evaluated 'fair';

FIG. 14A is a photograph without magnification, FIG. 14B is a photograph (×3.5), and FIG. 14C is a photograph (×18); FIG. 15A is a photograph without magnification, FIG. 15B is a photograph (×3.5), and FIG. 15C is a photograph (×18).

DESCRIPTION OF THE EMBODIMENTS

Figure 1:
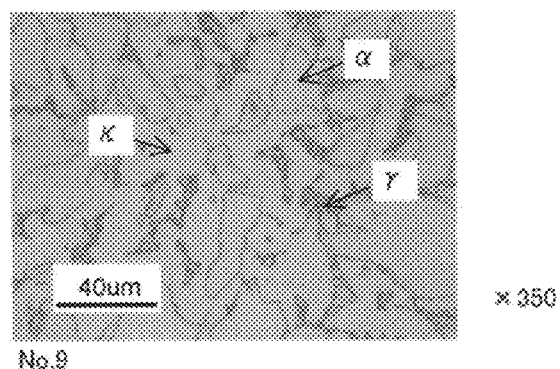
FIG. 1 is a photomicrograph (×350) showing a phase structure of Specimen No. 9 of embodiments.

First of all, the reason why the amount of each of alloy components composed of copper-based alloy castings of the invention is defined and the relationships of each of the components will be described.

Hereinafter, '%' of the alloy components means percent by mass.

Furthermore, the relationships are as follows;

| | |
|---|---|
| Cu−3.5×Si−3×P | Expression (1): |
| Cu−3.5×Si−3×P−0.5×[i]+0.5×[ii] | Expression (2): |
| Cu−3.5×Si−3×P−1.8×Al+a×Mn+0.5×Cr | Expression (3): |
| Cu−3.5×Si−3×P−0.5×[i]+0.5×[ii]−1.8×Al+a×Mn+0.5×Cr | Expression (4): |

Copper-based alloy castings according to the invention contain 69 to 88% of Cu, 2 to 5% of Si, 0.0005 to 0.04% of Zr and 0.01 to 0.25% of P, and the remainder is Zn and inevitable impurities.

Cu: 69 to 88%

Cu is the main component of the alloys. The grains are not necessarily refined in all copper-based alloy castings even when Zr and P are contained. The present inventor, as described below, found out that the grains can be refined considerably by adding a small amount of Zr when the amount of Si and P follow predetermined relationships.

In order to obtain various characteristics such as mechanical properties, corrosion resistance or the like as an industrial material, more than 69% of Cu is contained. However, if more than 88% of Cu is contained, the grain refinement is hindered, whereby the maximum amount of Cu is 88%. In addition, it is preferable to contain 70 to 84% of Cu, more preferable to contain 71 to 79.5% of Cu, and most preferable to contain 72 to 79% of Cu.

Si: 2 to 5%

Si decreases the stacking fault energy of the alloys and refines the grains considerably when contained with Zr, P, Cu, and Zn. In this case, 2% or more of Si must be contained. However, if more than 5% of Si is contained, the grain refinement saturates or tends to be hindered even when added with Cu and Zn. In addition, the ductility of the castings decreases. Also, the thermal conductivity decreases, and the solidification temperature range is widened, whereby the machinability deteriorates. Si also improves the fluidity of the molten alloy, prevents oxidation of the molten alloy, and decreases the melting point of the molten alloy. Furthermore, Si improves the corrosion resistance, particularly dezincification corrosion resistance and stress corrosion cracking resistance. Si also improves the machinability and the mechanical strength such as tensile strength, proof stress, impact strength, fatigue strength or the like. The above effects induce synergy effect for the grain refinement of the castings. It is preferable to contain 2.2 to 4.8% of Si, more preferable to contain 2.5 to 4.5% of Si, and most preferable to contain 2.7 to 3.7% of Si in order to induce the synergy effect.

Zr: 0.0005 to 0.04%

Zr is an important component for the grain refinement of the castings. As described below, if the amounts of Cu, Si and P follow predetermined relationships, the grains are effectively refined when 0.0005% or more of Zr is contained. The grains are refined more effectively at the amount of 0.0008% or more, most effectively at the amount of 0.0010% or more, and the grain refinement saturates at the amount of 0.0095%.

Meanwhile, the affinity of Zr to oxygen and sulfur is so strong that it is difficult to add Zr within a targeted narrow composition range. Therefore, considering that copper alloy castings are, in general, fabricated with recycled and scrapped materials in the air, a considerable amount of Zr must be added. Meanwhile, the inventor found out that, when 0.05% or more of Zr is contained in Cu—Zn—Si alloys, the grains are not being effectively refined during the melt-solidification. As a result, the maximum amount of Zr is defined at 0.04%. Zirconium oxide is easily formed in the casting and thus robust castings are difficult to obtain as the amount of Zr increases. In addition, since Zr is an expensive metal, it is not desired, from an economic viewpoint, to contain a large amount of Zr. Therefore, it is preferable to contain 0.0290% or less of Zr, more preferable to contain 0.0190%, and most preferable to contain 0.0095%, at which the grain refinement saturates, as described above. That is, considering the effect of Zr on matters other than the grain refinement, the optimal amount of Zr is 0.0010 to 0.0095%.

P: 0.01 to 0.25%.

P is, like Zr, an important component for the grain refinement of the castings. When contained with Zr, P refines the grains considerably. In addition, P increases the fluidity of the molten alloy, precipitates κ, γ and β-phases, to be described below, more finely, and improves the corrosion resistance. P shows the above effects when contained 0.01%. However, when P is contained too much, a low-melting point intermetallic compound is formed, and thus the alloy becomes brittle. Therefore, the maximum amount of P is defined at 0.25%, considering easy fabrication of the castings. Meanwhile, even though varying with the mixing ratio with the mixing amount of Zr and the mixing amount or ratio of Cu, Zn, Si of the matrix, the amount of P is preferably in the range of 0.02 to 0.20%, more preferably in the range of 0.03 to 0.16%, and most preferably in the range of 0.04 to 0.12%.

Zn: Remainder

Zn is a main component composing the copper-based alloy castings of the invention with Cu and Si. Zn decreases the stacking fault energy of the alloy and refines the grains of the castings. In addition, Zn induces the increase in the fluidity of the molten alloy, the decrease in the melting point, the prevention of Zr oxidation, the increase in corrosion resistance, and the increase in machinability. Furthermore, Zn improves the mechanical strength such as tensile strength, proof stress, impact strength, fatigue strength or the like. Therefore, Zn composes the alloy with the above components.

Meanwhile, Cu, Si and P among the components of the copper-based alloy castings of the invention are further required to satisfy the value of Expression (1): $Cu-3.5\times Si-3\times P$ is in the range from 60 to 71 as well as the above-mentioned conditions.

The expression is derived experimentally from the measured sizes of melt-solidified grains and conditions refining the grains of the copper-based alloy castings about 100 μm or less in the mean grain size. Even though Expression (1) will be described in detail later, it is preferable that Expression (1) have the value in the range of 62.5 to 68.5, and more preferable in the range of 64 to 67.

Furthermore, in the copper-based alloy castings of the invention, it is preferable that P/Zr be in the range of 0.8 to 250, Si/Zr be in the range of 80 to 6000, and Si/P be in the range of 12 to 220 in order to achieve the desired level of grain refinement.

P/Zr is preferably in the range of 1.5 to 150, more preferably in the range of 2 to 100, and most preferably in the range of 4 to 50. Si/Zr is preferably in the range of 100 to 5000, more preferably in the range of 120 to 3500, and most preferably in the range of 300 to 1500. Si/P is preferably in the range of 16 to 160, more preferably in the range of 20 to 120, and most preferably in the range of 25 to 80.

Meanwhile, on the assumption that Cu, Zn, Si, P, P/Zr, Si/Zr, Si/P, Expression (1) and phase structure are as claimed, Zr, particularly when added with P, increases the stacking fault density of a melt-solidified material and causes crystal nuclei to be generated faster than grain growth, whereby micronization of a melt-solidified material, specifically, the grains of the castings can be realized.

A second copper-based alloy casting according to the invention can further contain at least one element selected from a group consisting of 0.001 to 0.2% of Mg, 0.003 to 0.1% of B, 0.0002 to 0.01% of C, 0.001 to 0.2% of Ti and 0.01 to 0.3% of rare earth element, in addition to the components of the first copper-based alloy casting, as a grain refinement-promoting element.

Mg considerably decreases the loss of Zr due to sulfur and oxygen, which are mixed from recycled or scrapped materials such as inferior products, scrapped products, wire scrap, press scrap of copper alloy, chips, sprue runner generated during processing, sink head, lasher, mill ends or the like, and exists in the form of manganese sulfide and/or (manganese) oxide in the molten alloy so as to prevent the presence of Zr not contributing to the grain refinement, thereby contributing to the grain refinement. That is, if Mg is added before Zr, Mg becomes MgS and MgO, whereby Mg decreases the amount of S and O in the molten alloy and render Zr do its role effectively. Therefore, it is preferable to contain at least 0.001% of Mg in the alloy.

B, C, Ti and rare earth elements contribute to the grain refinement. Therefore, it is preferable to contain at least 0.003% of B, 0.0002% of C, 0.001% of Ti, and 0.01% of rare earth elements in order for the elements to effectively work. In this case, the rare earth elements (REM) mean fourteen kinds of lanthanoid elements, including La, Ce or the like as well as Sc and Y.

On the other hand, if Mg, B, C, Ti and rare earth elements are added too much, their effects saturate and the fluidity of the molten alloy deteriorates. Therefore, the maximum amounts of Mg, B, C, Ti and rare earth elements are defined at 0.2%, 0.1%, 0.01%, 0.2% and 0.3%, respectively.

In addition, the above elements are related with the effect of Zr on the grain refinement and influence Expression (1) of the first copper-based alloy casting, whereby, considering each of the effects of Mg, B, C, Ti and rare earth element, the amounts of the respective elements are adjusted to satisfy that the values of Expression (2): Cu−3.5×Si−3×P−0.5×[i]+0.5×[ii] are in the range of 60 to 71. In this case, [i] is a group composed of Mg and B, and [ii] is a group composed of C, Ti, and rare earth element.

A third copper-based alloy casting according to the invention can further contain at least one element selected from a group consisting of 0.02 to 1.5% of Al, 0.2 to 4.0% of Mn and 0.01 to 0.2% of Cr, in addition to the components of the first copper-based alloy casting, in order to increase the strength and wear resistance of the first copper-based alloy casting.

When containing the above elements, the alloys in which grains are refined have excellent strength and wear resistance.

Al strengthens the matrix so as to improve the strength and wear resistance. Therefore, it is preferable to contain 0.02% or more of Al, and more preferable to contain 0.1% or more of Al. However, if Al is contained too much, the elongation deteriorates, whereby the maximum amount of Al is defined at 1.5%.

Mn is combined with Si to form a Mn—Si intermetallic compound and contributes to improve the wear resistance. Therefore, it is preferable to contain 0.2% or more of Mn, and more preferable to contain 0.5% or more of Mn. However, if more than 4.0% of Mn is contained, the above effect saturates, and the fluidity of the molten alloy deteriorates, whereby Si, which is useful for the grain refinement, is consumed due to the formation of Mn—Si intermetallic compound. Therefore, the maximum amount of Mn is defined at 4.0%, and it is preferable to contain 3.5% or less of Mn.

Meanwhile, in order to suppress the consumption of Si, which is useful for the grain refinement, it is preferable that the amount of Si satisfy $2.3+⅓Mn≤Si≤3.5+⅓Mn$, and more preferable that it satisfy $2.6+⅓Mn≤Si≤3.4+⅓Mn$.

Cr is partially dissolved in the matrix and partially forms a fine intermetallic compound with Si so as to improve the wear resistance. Therefore, it is preferable to contain 0.01% or more of Cr. However, if Cr is contained too much, the Cr—Si compound is coarsened and the above effect saturates. Therefore, the maximum amount of Cr is defined at 0.2%.

In addition, Al, Mn and Cr are related with the effect of Zr on the grain refinement and influence Expression (1) of the first copper-based alloy casting. Therefore, considering the effect of Al, Mn and Cr, the amounts of the respective elements are adjusted to satisfy that the values of Expression (3): Cu−3.5×Si−3×P−1.8×Al+a×Mn+0.5Cr are in the range of 60 to 71. In this case, a=2 in a case that Mn is contained 0.5% or more and satisfies $0.2×Si≤Mn≤2.0×Si$, and a=0.5 in the other cases.

A fourth copper-based alloy casting according to the invention can further contain at least one element selected from a group consisting of 0.02 to 1.5% of Al, 0.2 to 4.0% of Mn and 0.01 to 0.2% of Cr, in addition to the components of the second copper-based alloy casting, in order to increase the strength and wear resistance of the second copper-based alloy casting.

As described above, the elements are related with the effect of Zr on the grain refinement and influence Expression (2) of the second copper-based alloy casting. Therefore, considering the effects of Al, Mn and Cr, the amounts of the respective elements are adjusted to satisfy that the values of Expression (4): Cu−3.5×Si−3×P−0.5×[i]+0.5×[ii]−1.8×Al+a×Mn are in the range of 60 to 71. In this case, a=2 in a case that Mn is contained 0.5% or more and satisfies $0.2×Si≤Mn≤2.0×Si$, and a=0.5 in the other cases.

First to fourth copper-based alloy castings can further contain at least one element selected from a group consisting of 0.1 to 2.5% of Sn, 0.02 to 0.25% of Sb and 0.02 to 0.25% of As as a corrosion resistance-improving element.

Containing the above elements can increase the corrosion resistance of the alloys in which grains are refined.

Sn improves erosion•corrosion resistance, seawater resistance. In particular, the synergy effect of Sn with Si forms Si and Sn-rich protective coatings in a corrosive liquid so as to lead to an excellent corrosion resistance. Therefore, it is preferable to contain 0.1% or more of Sn. However, if more than 2.5% of Sn is contained, segregations easily occur, and casting cracks easily occur since Sn is a low-melting point metal. In addition, the ductility deteriorates. Therefore, the maximum amount of Sn is defined at 2.5%, and it is preferable to contain in the range of 0.2 to 0.9% of Sn.

Sb and As improve dezincification corrosion resistance. Therefore, it is preferable to contain 0.02% or more of Sb and/or As. However, if Sb and/or As are contained too much, segregations easily occur, and casting cracks easily occur since Sb and As are low-melting point metals. In addition, the ductility may deteriorate. Therefore, the maximum amounts of Sb and As are defined 0.25% respectively.

In addition, the copper-based alloy castings according to the invention can further contain at least one element selected from a group consisting of 0.004 to 0.45% of Pb, 0.004 to 0.45% of Bi, 0.03 to 0.45% of Se and 0.01 to 0.45% of Te as a machinability-improving element.

When containing the above elements, the alloys in which grains are refined have excellent machinability.

The machinability can be improved by containing 0.004% of Pb, 0.004% of Bi, 0.03% of Se and/or 0.01% of Te.

Meanwhile, since Pb, Bi, Se and Te have negative influences on the human body, and Bi, Se and Te are rare elements, the maximum amounts of Pb, Bi, Se and Te are defined at 0.45% respectively. When the casting of the invention is used for valves for potable water, metal fitting for water-supplying and drainage or the like, it is preferable that the maximum amount of the above element be 0.2% or less.

In the copper-based alloy casting of the invention, it is allowed to contain impurities that are inevitably contained during the melting of raw material of the alloy. However, if Fe and Ni, as impurities, are contained too much, they consume Zr and P, which are useful for the grain refinement, so as to hinder the grain refinement. Therefore, when Fe and/or Ni is contained, amount thereof is defined at 0.5% or less. In addition, it is preferable to contain 0.25% or less of Fe and Ni, and more preferable to contain 0.15% or less of Fe and 0.2% or less of Ni.

In phase structures of the copper-based alloy castings of the invention, α, κ and γ-phases are adjusted to occupy 80% or more of the structure, and it is preferable that the above three phases be adjusted to occupy 100% of the structure. Meanwhile, the concentrations of Si in κ and γ-phases are higher than that in α-phase, and at least one of β, μ and δ-phases occupies the remainder when the three phases do not occupy 100% of the structure.

In order to obtain a phase structure, 80% or more of which are occupied by α, κ and γ-phases, it is required to optimize the casting conditions such as pouring temperature, cooling rate or the like. This is also a condition required to reduce the mean size of the melt-solidified grains to be about 100 μm or less.

In order to obtain an industrially satisfying machinability without addition of Pb, it is preferable that κ+γ-phase occupy 5 to 85% of the phase structure, and it is more preferable that the phase occupy 10 to 80% of the phase structure. On the other hand, when the other phases occupy more than 20% of the structure, a primary crystal is not α-phase, whereby the grain refinement cannot be achieved. In addition, machinability, corrosion-resistance, elongation and impact strength deteriorate. Particularly, in order to obtain excellent dezincification corrosion resistance, elongation and machinability, it is desirable that β-phase occupy 10% or less of the structure.

Hereinafter, the transformation of phase structure during the melt-solidification will be described in detail, since closely related with Expressions (1) to (4).

It is desirable that the primary crystal be α-phase during solidification. That is, if the solid phase is α-phase while the crystal nuclei are generated, the grain refinement is further expedited. In this case, the values of Expressions (1) to (4) are equivalent to 62.5. In addition, it is most preferable that the amount of α-phase primary crystal be 20 to 30% or more, and, in this case, the values of Expressions (1) to (4) are equivalent to 64. Furthermore, in the actual solidification process, if peritectic or eutectic reaction occurs during solidification, α-phase solid can exist in Cu—Zn—Si alloy when the solidification is complete, whereby the above fact becomes a condition for the grain refinement, and the values of Expressions (1) to (4) are equivalent to 62.5. Even though the mean grain size is large even at compositions having the values close but not equal to 62.5, the grains are refined. Then, Expressions (1) to (4) have values of 60 as the minimum.

Meanwhile, Expressions (1) to (4) have the values of 71 due to the following facts: the grain refinement becomes more difficult as the amount of added Zn decreases, peritectic reaction does not occur in a practical non-equilibrium state during solidification, and the machinability deteriorates. In addition, the solidification temperature range is widened. If the solidification temperature range is widened, solid-phase granular coalescences are easily generated, and thus dendrites have shapes similar to a tree. Furthermore, even though the grains are refined to a certain degree, cracks and cavities easily occur, and the number and size of shrinkage cavities and shrinkage cavities increase.

The grains are best refined when phases other than α-phase, mainly β, κ or γ-phase are crystallized or precipitated after solidification. That is, as the number of α-phase primary crystals increases, the grains are coalesced with one another, whereby the primary crystals are shaped like dendrites having grown arms. If phases other than α-phase such as β, γ and κ-phase are crystallized or precipitated in order to prevent the above phenomenon, the growth of α-phase grains during solidification and cooling from high temperature are suppressed, and thus micronization can be realized. For example, if eutectic reaction occurs during solidification, the micronization of grains can be realized. In order for the second phase to exist during solidification, it is desirable that the values of Expressions (1) to (4) have 68.5 or less, most desirable that they have 67, considering the balance with α-phase and the solidification temperature.

Meanwhile, in order to obtain mechanical properties such as ductility, impact strength, dezincification corrosion resistance, stress corrosion cracking resistance and machinability, the values of Expressions (1) to (4) are required to be 60 or more, and it is preferable that the values be 62.5 or more, more preferable that the values be 64 or more. On the other hand, in order to obtain high strength and wear resistance as well as excellent machinablity, the values of Expressions (1) to (4) are required to be 71 or less, and it is preferable that the values be 68.5 or less. Furthermore, in order to obtain an industrially satisfactory machinability without Pb contained, it is most preferable that the values be 67 or less.

The copper-based alloy casting according to the invention with a phase structure, more than 80% of which is occupied by α, κ and γ-phases, can be obtained by the following casting conditions.

First, the maximum pouring temperature is, in general, 1150° C. or less or liquidus temperature+250° C. or less, preferably 1100° C. or less, and most preferably 1050° C. or less. The minimum pouring temperature is not specified as long as the molten alloy can reach every corner of the mold. However, in general, the minimum pouring temperature is in the range of 900 to 950° C., right above the liquidus temperature. It should be understood that the above temperature varies with the compositions of the alloys.

As described above, the phase structure has a close relationship with the above expressions, and the temperature range from solidification-complete temperature to 500° C. has the biggest effect on the phase transformation. When the above expressions have the values of 62.5 or less, it is difficult to obtain a phase structure, more than 80% of which is occupied by α, κ and γ-phases, if the alloy is cooled at the average rate of 250° C./second or more. It is preferable to cool the alloy at the rate of 100° C./second or less when the expressions have the values of 62.5 or less. Meanwhile, if the above expressions have the values of 68.5 or more, and the alloy is cooled at the average rate of 0.5° C./second or less in the temperature range of 700 to 800° C., even though α, κ and γ-phases occupy more than 80% of the phase structure, the precipitations of κ and γ-phases are hindered, and thus α-phase grains are grown, whereby it become more difficult to achieve the grain refinement. Therefore, it is preferable to cool the alloy at the rate of 1° C./minute, at least, in the temperature range of 700 to 800° C. even when the expressions have the values of 68.5 or more.

It is needless to say that, in the alloys of the invention, the grains can be refined by common methods or means for casting refinement, that is, the decrease in pouring temperature, fastening the cooling rate, stirring during solidification or the like.

In the specification, the word 'casting' means a substance, which is wholly or partially melted and solidified. The casting includes various substances, beginning with ingot, slab, billet for rolling or extrusion, for example, castings by virtue of sand casting, metal casting, low-pressure casting, diecast, lost wax, semi-solid casting (for example, Thixo casting, Rheocasting), squeeze, centrifugal casting, continuous casting (for example, horizontal continuous casting, metallizing, build-up spraying or upward, rod manufactured by upCast, hollow rod, heteromorphic rod, heteromorphic hollow rod, coil material, wire material or the like), melting and forging (direct forging), metallizing, build-up spraying, lining, overlay. Also, in a broad sense, welding should be included in the casting because part of the base material is melted, solidified and combined together in welding.

Embodiment

Alloy materials having compositions shown in Tables 1 to 3 are melted in an electric furnace and poured into a metal mold in order to obtain specimens. The pouring temperature is 1000° C., and the pre-heating temperature of the metal mold is 200° C. The specimens are cylindrical, 40 mm in diameter and 280 mm in length.

The area ratios of respective phases composing the phase structure of the specimens are measured. Also, the cylindrical specimens are cut parallel to the bottom surface at 100 mm away from the bottom surface, and the mean grain sizes are measured at 10 mm away from the center of the cross-sectional surface of the specimen. The mean grain sizes are measured on the basis of the comparative methods for estimating average grain size of wrought copper and copper alloy of JIS H0501, in which, after the cut surfaces are etched by nitric acid, grains as large as 0.5 mm and more are observed with the naked eye or a magnifying glass offering 5 times the magnification, and grains smaller than 0.5 mm are etched by a mixed solution of hydrogen peroxide and ammonia water and then observed with an optical microscope. Meanwhile, the grain sizes are measured at 10 mm away from the axis of the cut surface and 100 mm away from the bottom surface.

Tables 1 to 3 disclose the measured grain sizes. Specimens No. 1 to 44 disclosed in Tables 1 and 2 are embodiments of the invention, and Specimens No. 101 to 122 disclosed in Table 3 are comparative examples. Among the comparative examples, bold-lettered data illustrate that the specimens do not follow the conditions defined for the copper-based alloy casting of the invention.

TABLE 1

| | Chemical composition of alloys (remainder Zn and inevitable impurities) (mass %) | | | | | | | | | | | Expression | | Area ratio of phase structure (%) | | Mean grain size |
|---|---|---|---|---|---|---|---|---|---|---|---|---|---|---|---|---|
| No. | Cu | Si | Zr | P | Mg, B, C, Ti, REM | Al, Mn, Cr | Sn, Sb, As | Pb, Bi, Se, Te | P/Zr | Si/Zr | Si/P | type | value | α + κ + γ | others | (μm) |
| 1 | 71.0 | 2.93 | 0.0150 | 0.10 | — | — | — | — | 6.7 | 195 | 29 | (1) | 60.4 | 85 | 15 | 100 |
| 2 | 74.2 | 3.73 | 0.0160 | 0.10 | — | — | — | — | 6.3 | 495 | 78 | (1) | 60.8 | 85 | 15 | 90 |
| 3 | 70.3 | 2.50 | 0.0120 | 0.12 | — | — | — | — | 10.0 | 208 | 21 | (1) | 61.2 | 90 | 10 | 80 |
| 4 | 72.0 | 2.54 | 0.0155 | 0.07 | — | — | — | — | 4.5 | 164 | 36 | (1) | 62.9 | 95 | 5 | 65 |
| 5 | 74.7 | 3.50 | 0.0180 | 0.09 | — | — | — | — | 5.0 | 194 | 39 | (1) | 63.9 | 100 | 0 | 30 |
| 6 | 75.3 | 2.98 | 0.0007 | 0.09 | — | — | — | — | 129 | 4257 | 33 | (1) | 64.6 | 100 | 0 | 85 |
| 7 | 75.8 | 3.10 | 0.0190 | 0.08 | — | — | — | — | 4.2 | 163 | 39 | (1) | 64.7 | 100 | 0 | 30 |
| 8 | 75.9 | 3.08 | 0.0053 | 0.06 | — | — | — | — | 11.3 | 581 | 51 | (1) | 64.9 | 100 | 0 | 25 |
| 9 | 75.8 | 3.00 | 0.0100 | 0.10 | — | — | — | — | 10 | 300 | 30 | (1) | 65.0 | 100 | 0 | 15 |
| 10 | 76.1 | 3.10 | 0.0290 | 0.07 | — | — | — | — | 2.4 | 107 | 44 | (1) | 65.0 | 100 | 0 | 35 |
| 11 | 76.2 | 3.10 | 0.0017 | 0.07 | — | — | — | — | 58 | 2583 | 44 | (1) | 65.1 | 100 | 0 | 50 |
| 12 | 76.3 | 3.09 | 0.0185 | 0.07 | — | — | — | — | 3.8 | 167 | 44 | (1) | 65.3 | 100 | 0 | 25 |
| 13 | 76.1 | 3.00 | 0.0038 | 0.13 | — | — | — | — | 3.4 | 79 | 23 | (1) | 65.2 | 100 | 0 | 80 |
| 14 | 76.6 | 3.07 | 0.0040 | 0.08 | — | — | — | — | 20 | 768 | 38 | (1) | 65.6 | 100 | 0 | 20 |
| 15 | 81.0 | 3.80 | 0.0170 | 0.06 | — | — | — | — | 3.5 | 224 | 63 | (1) | 67.5 | 100 | 0 | 50 |
| 16 | 75.8 | 2.27 | 0.0280 | 0.08 | — | — | — | — | 2.9 | 81 | 28 | (1) | 67.6 | 100 | 0 | 65 |
| 17 | 83.1 | 4.21 | 0.0230 | 0.03 | — | — | — | — | 1.3 | 183 | 140 | (1) | 68.3 | 100 | 0 | 70 |
| 18 | 79.2 | 2.76 | 0.0210 | 0.16 | — | — | — | — | 7.6 | 131 | 17 | (1) | 69.1 | 100 | 0 | 75 |
| 19 | 80.2 | 2.70 | 0.0230 | 0.07 | — | — | — | — | 3.0 | 117 | 39 | (1) | 70.5 | 100 | 0 | 80 |
| 20 | 79.4 | 2.30 | 0.0160 | 0.11 | — | — | — | — | 6.9 | 144 | 21 | (1) | 71.0 | 100 | 0 | 90 |
| 21 | 76.9 | 3.20 | 0.0009 | 0.08 | Mg: 0.004 | — | — | — | 88.9 | 3556 | 40 | (2) | 65.5 | 100 | 0 | 40 |
| 22 | 75.8 | 2.98 | 0.0032 | 0.07 | Mg: 0.11 | — | — | — | 21.9 | 931 | 43 | (2) | 65.2 | 100 | 0 | 20 |
| 23 | 73.8 | 2.76 | 0.0075 | 0.12 | B: 0.011 | — | — | — | 16.0 | 368 | 23 | (2) | 63.8 | 100 | 0 | 20 |
| 24 | 77.3 | 3.41 | 0.0110 | 0.09 | C: 0.001 | — | — | — | 8.2 | 310 | 38 | (2) | 65.1 | 100 | 0 | 15 |
| 25 | 75.9 | 3.00 | 0.0130 | 0.11 | Ti: 0.012 | — | — | — | 8.5 | 231 | 27 | (2) | 65.1 | 100 | 0 | 15 |

Reference: * Expressions (1) Cu − 3.5 × Si − 3 × P
(2) Cu − 3.5 × Si − 3 × P − 0.5 × [i] + 0.5 × [ii]
(3) Cu − 3.5 × Si − 3 × P − 1.8 × Al + a × Mn + 0.5 × Cr
(4) Cu − 3.5 × Si − 3 × P − 0.5 × [i] + 0.5 × [ii] − 1.8 × Al + a × Mn + 0.5 × Cr

TABLE 2

| | Chemical composition of alloys (remainder Zn and inevitable impurities) (mass %) | | | | | | | | | | | Expression | | Area ratio of phase structure (%) | | Mean grain size |
|---|---|---|---|---|---|---|---|---|---|---|---|---|---|---|---|---|
| No. | Cu | Si | Zr | P | Mg, B, C, Ti, REM | Al, Mn, Cr | Sn, Sb, As | Pb, Bi, Se, Te | P/Zr | Si/Zr | Si/P | type | value | α + κ + γ | others | (μm) |
| 26 | 76.6 | 3.12 | 0.0150 | 0.08 | REM: 0.05 | — | — | — | 5.3 | 208 | 39 | (2) | 65.4 | 100 | 0 | 20 |
| 27 | 75.2 | 3.12 | 0.0035 | 0.09 | — | Mn: 0.4 | — | — | 26 | 891 | 35 | (3) | 64.2 | 100 | 0 | 30 |
| 28 | 70.9 | 4.53 | 0.0085 | 0.17 | — | Mn: 3.6 | — | — | 20 | 533 | 27 | (3) | 61.7 | 95 | 5 | 40 |
| 29 | 73.3 | 4.02 | 0.0120 | 0.15 | — | Al: 0.5 Mn: 2.7 | — | — | 13 | 335 | 27 | (3) | 63.3 | 100 | 0 | 25 |

TABLE 2-continued

| | Chemical composition of alloys (remainder Zn and inevitable impurities) (mass %) | | | | | | | | | | | Expression | | Area ratio of phase structure (%) | | Mean grain size (μm) |
|---|---|---|---|---|---|---|---|---|---|---|---|---|---|---|---|---|
| No. | Cu | Si | Zr | P | Mg, B, C, Ti, REM | Al, Mn, Cr | Sn, Sb, As | Pb, Bi, Se, Te | P/Zr | Si/Zr | Si/P | type | value | α + κ + γ | others | |
| 30 | 75.3 | 3.65 | 0.0160 | 0.10 | — | Al: 0.9 Mn: 0.9 | — | — | 6 | 228 | 37 | (3) | 62.4 | 100 | 0 | 35 |
| 31 | 75.6 | 3.13 | 0.0240 | 0.10 | C: 0.0006 | Cr: 0.2 | — | — | 4 | 130 | 31 | (4) | 64.4 | 100 | 0 | 30 |
| 32 | 74.9 | 2.89 | 0.0035 | 0.11 | — | — | Sn: 0.15 | — | 31 | 826 | 26 | (1) | 64.5 | 100 | 0 | 25 |
| 33 | 78.4 | 3.12 | 0.0140 | 0.08 | — | — | Sn: 1.4 | — | 6 | 223 | 39 | (1) | 67.2 | 100 | 0 | 15 |
| 34 | 78.8 | 3.76 | 0.0035 | 0.13 | — | — | Sb: 0.03 | — | 37 | 1074 | 29 | (1) | 65.2 | 100 | 0 | 30 |
| 35 | 76.5 | 3.11 | 0.0015 | 0.03 | — | — | As: 0.13 | — | 20 | 2073 | 104 | (1) | 65.5 | 100 | 0 | 50 |
| 36 | 76.8 | 3.12 | 0.0230 | 0.08 | — | — | — | Pb: 0.08 | 3 | 136 | 39 | (1) | 65.7 | 100 | 0 | 30 |
| 37 | 76.2 | 3.08 | 0.0125 | 0.07 | — | — | — | Bi: 0.06 | 6 | 246 | 44 | (1) | 65.2 | 100 | 0 | 25 |
| 38 | 75.6 | 2.99 | 0.0180 | 0.05 | — | — | — | Bi: 0.3 Se: 0.3 | 3 | 166 | 60 | (2) | 65.0 | 100 | 0 | 25 |
| 39 | 76.7 | 3.06 | 0.0180 | 0.12 | — | — | Sn: 0.6 | Pb: 0.015 | 6 | 170 | 28 | (1) | 65.7 | 100 | 0 | 20 |
| 40 | 82.3 | 3.80 | 0.0150 | 0.04 | — | Al: 1.2 | — | Bi: 0.25 | 3 | 253 | 95 | (3) | 66.7 | 100 | 0 | 25 |
| 41 | 73.2 | 3.82 | 0.0095 | 0.12 | Mg: 0.008 | Mn: 1.9 | — | Pb: 0.19 | | | | (4) | 66.3 | 100 | 0 | 20 |
| 42 | 74.5 | 3.98 | 0.0055 | 0.09 | Mg: 0.032 | Al: 0.04 Mn: 2.9 | Sn: 0.8 | — | 15 | 727 | 44 | (4) | 66.0 | 100 | 0 | 15 |
| 43 | 78.8 | 3.22 | 0.0110 | 0.08 | — | Al: 1.2 | Sb: 0.09 | — | 7 | 293 | 40 | (3) | 65.1 | 100 | 0 | 15 |
| 44 | 74.7 | 3.50 | 0.0180 | 0.09 | — | Al: 0.2 Mn: 1.1 | — | Pb: 0.15 | 5 | 194 | 39 | (3) | 64.0 | 100 | 0 | 30 |

Reference: * Expressions (1) Cu − 3.5 × Si − 3 × P
(2) Cu − 3.5 × Si − 3 × P − 0.5 × [i] + 0.5 × [ii]
(3) Cu − 3.5 × Si − 3 × P − 1.8 × Al + a × Mn + 0.5 × Cr
(4) Cu − 3.5 × Si − 3 × P − 0.5 × [i] + 0.5 × [ii] − 1.8 × Al + a × Mn + 0.5 × Cr

TABLE 3

| | Chemical composition of alloys (remainder Zn and inevitable impurities) (mass %) | | | | | | | | | | | | Expression | | Area ratio of phase structure (%) | | Mean grain size (μm) |
|---|---|---|---|---|---|---|---|---|---|---|---|---|---|---|---|---|---|
| No. | Cu | Si | Zr | P | Mg, B, C, Ti, REM | Al, Mn, Cr | Sn, Sb, As | Pb, Bi, Se, Te | Fe, Ni | P/Zr | Si/Zr | Si/P | type | value | α + κ + γ | others | |
| 101 | 70.2 | 4.45 | 0.0100 | 0.08 | — | — | — | — | — | 8.0 | 445 | 56 | (1) | 54.4 | 60 | 40 | 1500 |
| 102 | 73.0 | 3.98 | 0.0150 | 0.10 | — | — | — | — | — | 6.7 | 265 | 40 | (1) | 58.8 | 65 | 35 | 800 |
| 103 | 70.3 | 3.08 | 0.0310 | 0.10 | — | — | — | — | — | 3.2 | 99 | 31 | (1) | 59.2 | 60 | 40 | 800 |
| 104 | 69.3 | 2.64 | 0.0170 | 0.11 | — | — | — | — | — | 6.5 | 155 | 24 | (1) | 59.7 | 70 | 30 | 600 |
| 105 | 79.5 | 2.10 | 0.0030 | 0.07 | — | — | — | — | — | 23.3 | 700 | 30 | (1) | 71.9 | 95 | 5 | 300 |
| 106 | 86.0 | 4.12 | 0.0290 | 0.09 | — | — | — | — | — | 3.1 | 142 | 46 | (1) | 71.3 | 100 | 0 | 200 |
| 107 | 82.5 | 2.56 | 0.0120 | 0.08 | — | — | — | — | — | 6.7 | 213 | 32 | (1) | 73.3 | 100 | 0 | 250 |
| 108 | 82.7 | 2.25 | 0.0055 | 0.10 | — | — | — | — | — | 4.2 | 93 | 22 | (1) | 74.5 | 100 | 0 | 300 |
| 109 | 79.8 | 4.05 | — | — | — | — | — | — | — | — | — | — | (1) | 65.6 | 100 | 0 | 2000 |
| 110 | 76.2 | 3.12 | 0.0003 | 0.09 | — | — | — | — | — | 300 | 10400 | 35 | (1) | 65.0 | 100 | 0 | 500 |
| 111 | 76.1 | 3.07 | 0.0002 | 0.07 | — | — | — | — | — | 350 | 15350 | 44 | (1) | 65.1 | 100 | 0 | 600 |
| 112 | 74.7 | 2.95 | 0.0500 | 0.09 | — | — | — | — | — | 1.8 | 59 | 33 | (1) | 64.1 | 100 | 0 | 150 |
| 113 | 72.8 | 2.35 | 0.1500 | 0.08 | — | — | — | — | — | 0.5 | 16 | 29 | (1) | 65.5 | 100 | 0 | 200 |
| 114 | 79.3 | 4.05 | 0.3000 | 0.03 | — | — | — | — | — | 0.1 | 14 | 135 | (1) | 66.4 | 100 | 0 | 200 |
| 115 | 75.6 | 3.18 | 0.0050 | 0.005 | — | — | — | — | — | 1.0 | 636 | 64 | (1) | 64.5 | 100 | 0 | 350 |
| 116 | 70.2 | 1.70 | 0.0060 | 0.08 | — | — | — | — | — | 13.3 | 283 | 21 | (1) | 64.0 | 95 | 5 | 200 |
| 117 | 85.8 | 5.50 | 0.0110 | 0.10 | — | — | — | — | — | 9.1 | 500 | 55 | (1) | 66.3 | 100 | 0 | 200 |
| 118 | 76.6 | 3.11 | 0.0180 | 0.09 | — | — | — | — | Fe: 0.55 | 5.0 | 173 | 35 | (1) | 65.4 | 100 | 0 | 400 |
| 119 | 75.8 | 3.05 | 0.0170 | 0.09 | — | — | — | — | Ni: 0.6 | 5.3 | 179 | 34 | (1) | 64.9 | 100 | 0 | 600 |
| 120 | 70.1 | 2.77 | 0.0180 | 0.08 | — | — | — | — | — | 4.4 | 154 | 35 | (1) | 60.2 | 75 | 25 | 500 |
| 121 | 72.9 | 3.45 | 0.0150 | 0.15 | — | — | — | — | — | 10.0 | 230 | 23 | (1) | 60.4 | 75 | 25 | 400 |
| 122 | 76.5 | 3.05 | — | 0.08 | — | — | Sn: 0.6 | Pb: 0.015 | — | — | — | — | (2) | 65.6 | 100 | 0 | 1500 |

Reference: * Expressions (1) Cu − 3.5 × Si − 3 × P
(2) Cu − 3.5 × Si − 3 × P − 0.5 × [i] + 0.5 × [ii]
(3) Cu − 3.5 × Si − 3 × P − 1.8 × Al + a × Mn + 0.5 × Cr
(4) Cu − 3.5 × Si − 3 × P − 0.5 × [i] + 0.5 × [ii] − 1.8 × Al + a × Mn + 0.5 × Cr First, the phase structure will be described.

Specimens No. 1 to 3 of the embodiments and Specimens No. 120 and 121 of the comparative examples have almost the same values for the expressions, and the results disclose that the mean grain sizes decrease as the total area ratios of α, κ and γ-phases increase. It can be found out that the above three phases should occupy more than 80% of the phase structure in order to refine the grains as small as 100 μm or less, which is an object of the invention.

Figure 2:
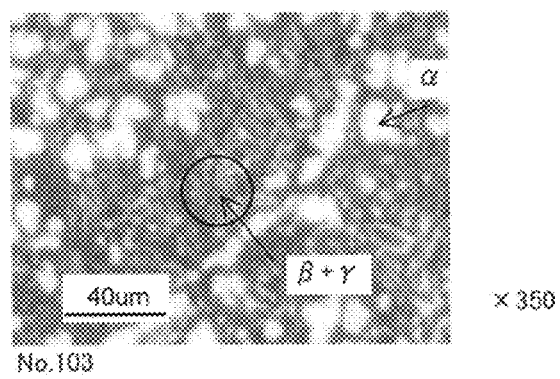
FIG. 2 is a photomicrograph (×350) showing a phase structure of Specimen No. 103 of comparative examples.
Figure 3:
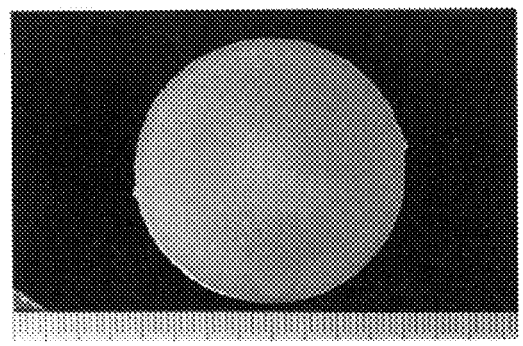
FIG. 3 is macro photograph and photomicrograph (×75) showing a metal structure of a cross section of Specimen No. 9 of the embodiments.
Figure 3:
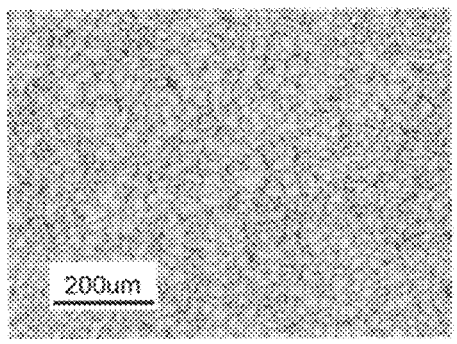
Figure 4:
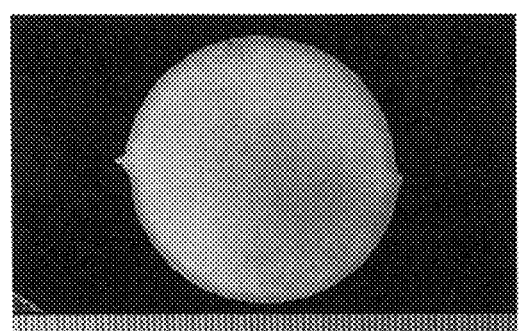
FIG. 4 is macro photograph and photomicrograph (×75) showing a metal structure of a cross section of Specimen No. 10 of the embodiments.
Figure 4:
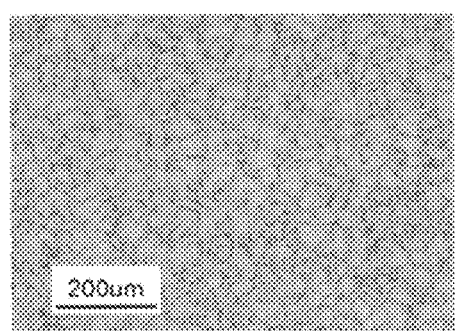
Figure 5:
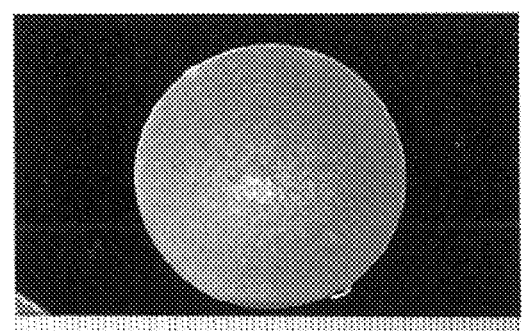
FIG. 5 is macro photograph and photomicrograph (×75) showing a metal structure of a cross section of Specimen No. 6 of the embodiments.
Figure 5:
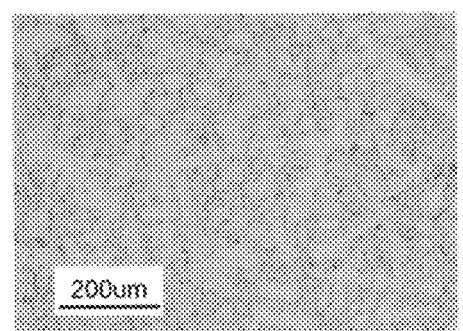
Figure 6:
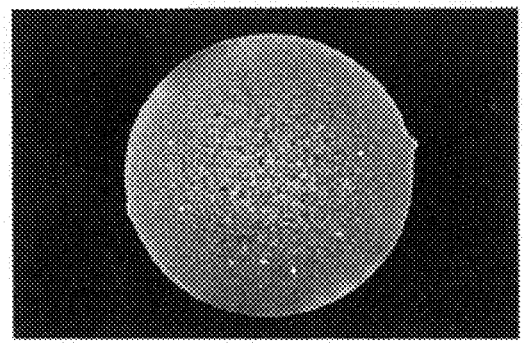
FIG. 6 is macro photograph and photomicrograph (×75) of a metal structure showing a cross section of Specimen No. 112 of the comparative examples.
Figure 6:
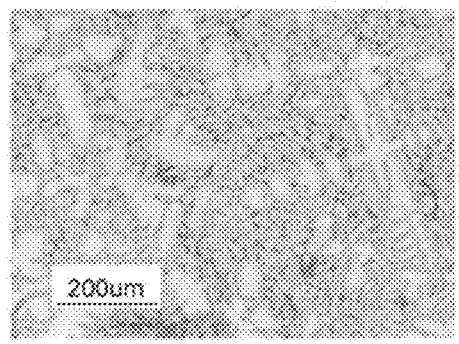
Figure 7:
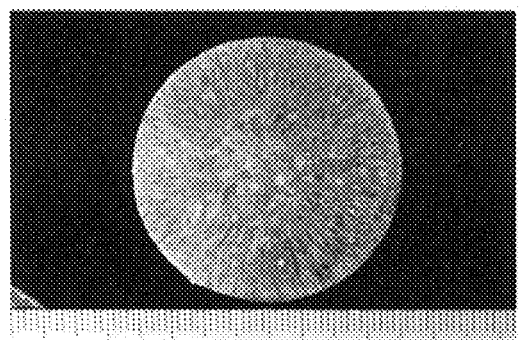
FIG. 7 is macro photograph and photomicrograph (×75) showing a metal structure of a cross section of Specimen No. 110 of the comparative examples.
Figure 7:
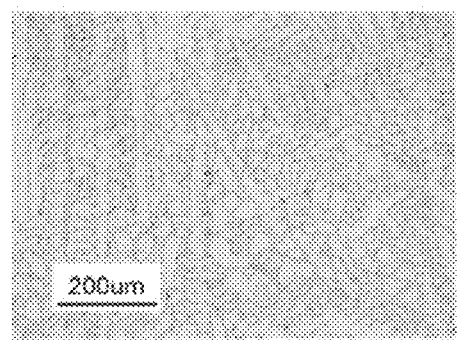
Figure 8:
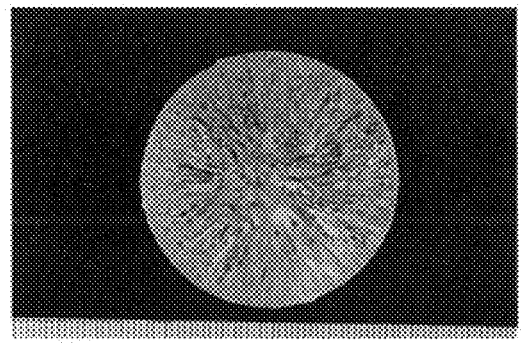
FIG. 8 is macro photograph and photomicrograph (×75) showing a metal structure of a cross section of Specimen No. 103 of the comparative examples.
Figure 8:
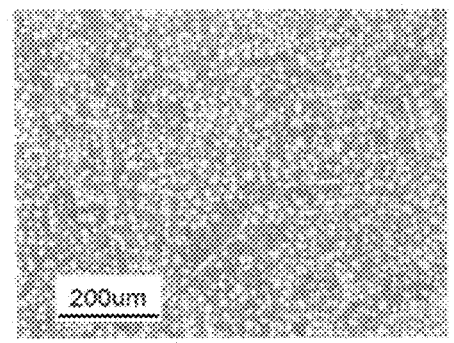

In addition, the phase structures of Specimen No. 9 of the embodiments and Specimen No. 103 of the comparative examples are disclosed in FIGS. 1 and 2. In FIG. 1, α, κ and γ-phases occupy 100% of the phase structure, and the mean grain size is 15 μm. In FIG. 2, α, κ and γ-phases occupy 60% of the phase structure with β-phase occupying the remainder, and the mean grain size is 800 μm.

It is evident from Tables 1 and 2 that the mean grain size is refined as small as 100 μm or less after melt-solidification if the amount of Zr, the values of the expressions, the area ratios of α, κ and γ-phases satisfy the conditions defined for the invention.

In Specimens No. 101 to 104 of the comparative examples, the expressions have values of less than 60, the total area ratios of the above three phases are less than 80%, and the mean grain sizes are considerably large.

In Specimens No. 105 to 108 of the comparative examples, the expressions have values of larger than 71. Even though the other conditions defined for the invention are satisfied, the mean grain sizes are 200 μm or larger.

In Specimens No. 120 and 121 of the comparative examples, even though the total area ratios of the three phases are less than 80% and the values of the expressions approaches the minimum defined for the invention, the mean grain sizes are 400 μm or larger.

Specimen No. 109 of the comparative examples contains no Zr and P, and Specimens No. 110 and 111 of the comparative examples contain a smaller amount of Zr than that defined for the invention. Meanwhile, since Specimens No. 110 and 111 of the comparative examples contain a small amount of Zr, the values of Si/Zr and P/Zr are not in the preferable ranges of the invention, and thus the mean grain sizes are considerably large.

Specimens No. 113 to 115 of the comparative examples contain larger amounts of Zr than that defined for the invention, and it can be found out that the grain refinement is hindered if more than 0.05% of Zr is contained.

Figure 9A:
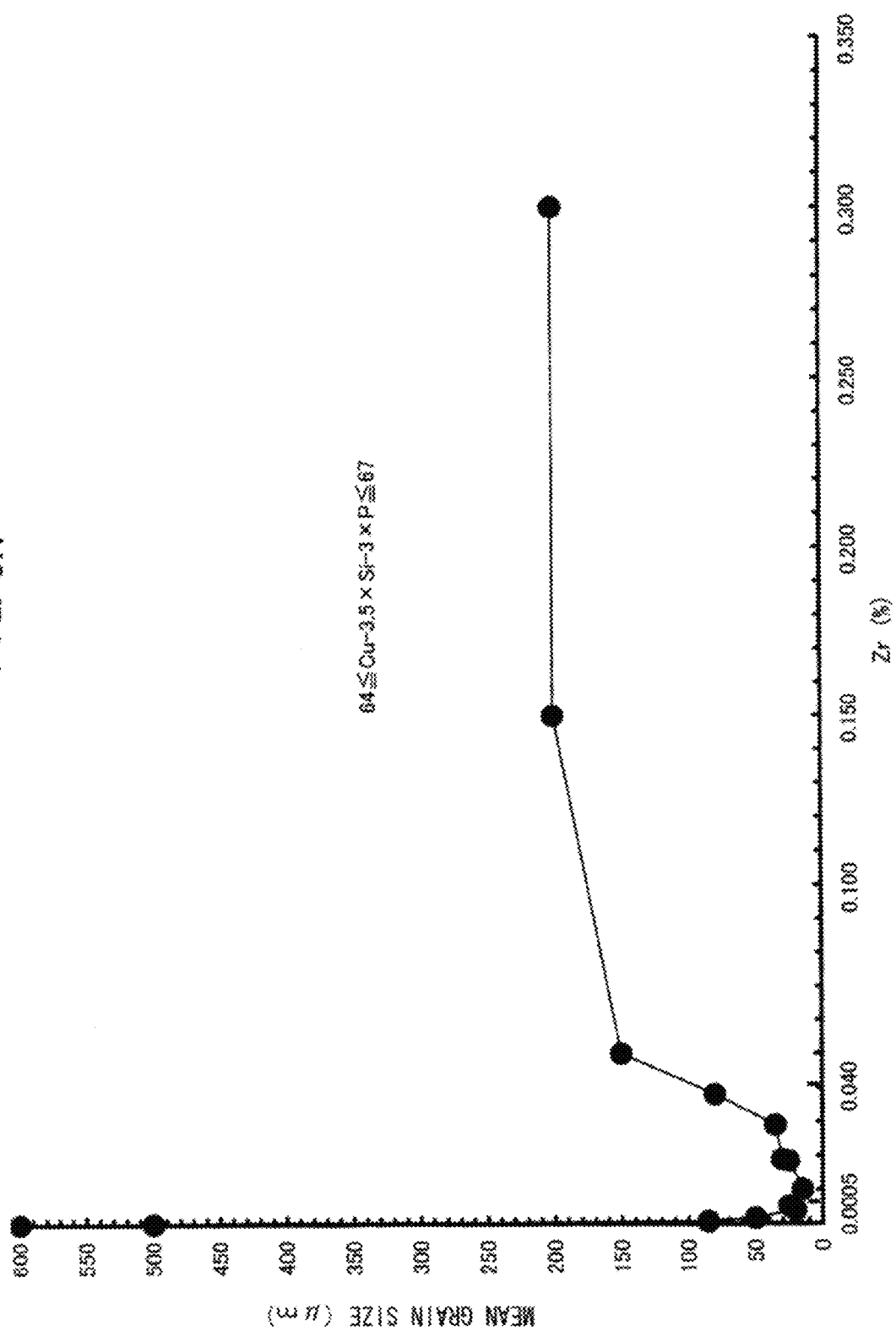
FIG. 9A is a graph showing a relationship between the amount of Zr and the mean grain size within the extent of 64≤Cu−3.5×Si−3×P≤67.

FIGS. 9A and 9B show the relationship of the mean grain size with the amount of Zr for the specimens of the embodiments (Cu, Si, Zr, P and the remainder Zn), for which the expressions have the values in the preferable range of 64 to 67, and Specimens No. 110 to 115 of the comparative examples. In FIGS. 9A and 9B, the values of the expressions are limited within the range shown in the figures because, as shown in Specimens No. 1 to 4 and No. 15 to 20 of the embodiment, the values of the expressions considerably influence the mean grain sizes outside the limited range. Therefore, in the limited range, the mean grain sizes are estimated without influence by the values.

Specimen No. 115 of the comparative examples contains a smaller amount of P than that defined for the invention. Also, in Specimens No. 116 and 117 of the comparative examples, the amounts of Si are not in the defined range of the invention, and the mean grain sizes are 200 μm or more.

Specimens No. 118 and 119 of the comparative examples illustrate that the mean grain size increase when Fe and Ni are contained more than defined for the invention as impurities.

Figure 10:
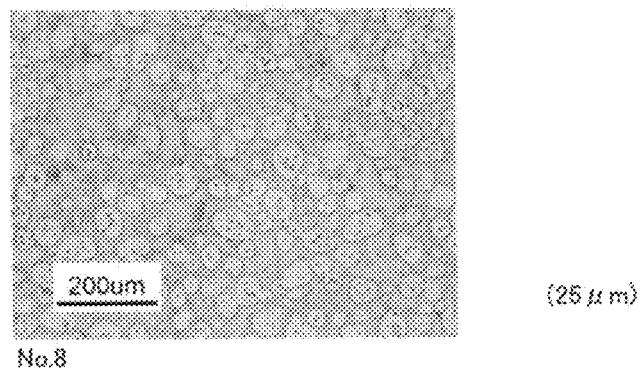
FIG. 10 is a photomicrograph (×75) showing the shape of dendrite in Specimen No. 8 of the comparative example.
Figure 11:
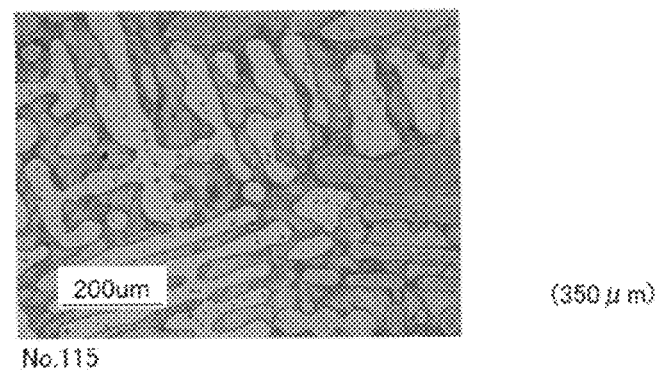
FIG. 11 is a photomicrograph (×75) showing the shape of dendrite in Specimen No. 115 of the comparative example.
Figure 12:
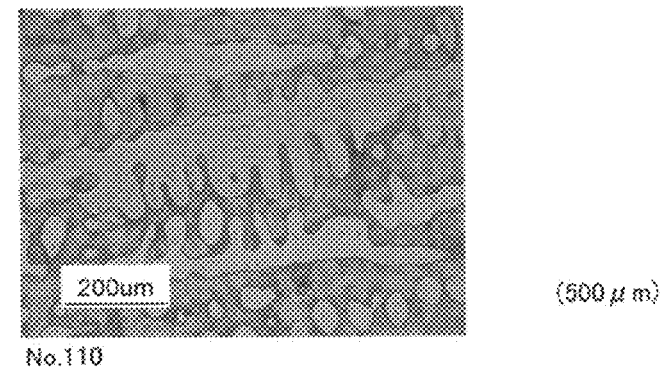
FIG. 12 is a photomicrograph (×75) showing the shape of dendrite in Specimen No. 110 of the comparative example.

FIGS. 10 to 12 illustrate respectively the metal structures of Specimen No. 8 of the embodiments (25 μm in the mean grain size), Specimens No. 115 (350 μm in the mean grain size) and 110 (500 μm in the mean grain size) of the comparative examples that are cooled during solidification process, specifically at which 40% solid-phases and 60% liquid-phases coexist (semi-molten state), and then etched.

During solidification (melt-solidification), in Specimen No. 8 of the embodiments, the arms of dendrites are not generated, and thus the dendrites have a circular or oval shape, contrary to the above, in Specimens No. 115 and 110 of the embodiments, dendrites have a tree-shape. Like the above, in Specimen No. 8 of the embodiments, crystal nuclei are generated faster than grain growth (growth of the arms of dendrites), whereby the grains can be refined (the matrix is a liquid phase in the semi-molten state).

The above fact illustrates that the copper-based alloy casting of the invention is preferable for semi-solid casting, and if the solid phase is granular, both liquid and solid phases can reach every corner of the metal mold without substantial resistance.

Figure 13A:
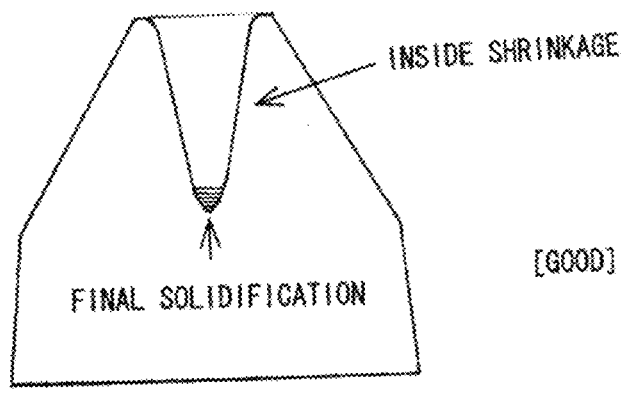
FIGS. 13A to 13C are views showing final solidificaton portions in Tatur Shrinkage Test.
Figure 13B:
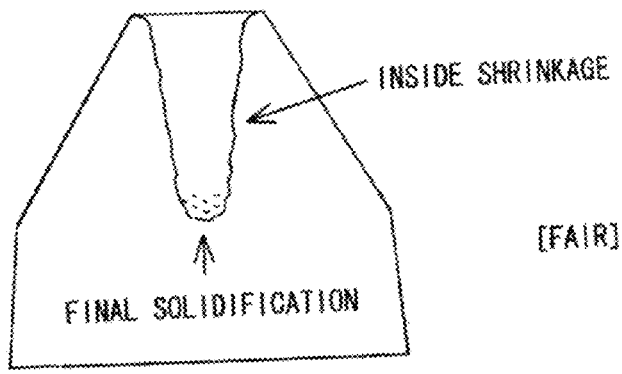
Figure 13C:
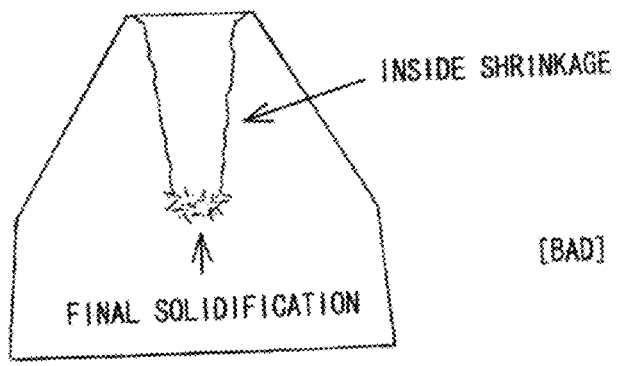

In order to evaluate the castability of the copper-based alloy castings of the invention, in which the grains are refined, Tatur Shrinkage Test is performed on the specimens illustrated in Table 4, and the shapes of the inside shrinkages and the existence of defects such as porosity, hole, cavity or the like in the vicinity of the inside shrinkages is examined. The castability is evaluated 'good' for specimens with smooth shapes of the inside shrinkages and no defects such as porosity or the like at the final solidification portion as shown in FIG. 13A, 'fair' for specimens with non-smooth shapes of the inside shrinkages and some defects such as porosity or the like at the final solidification portion as shown in FIG. 13B, and 'bad' for specimens with uneven shapes of the inside shrinkage and obvious defects such as porosity or the like at the final solidification portion as shown in FIG. 13C. Table 4 illustrates the test result.

TABLE 4

| Specimen No. | Mean grain size | Tatur shrinkage test |
|---|---|---|
| 6 | 85 μm | Good |
| 9 | 15 μm | Good |
| 102 | 800 μm | Bad |
| 108 | 300 μm | Bad |
| 109 | 2000 μm | Bad |
| 110 | 500 μm | Fair |
| 113 | 200 μm | Fair |

As illustrated in Table 4, Specimens No. 6 and 9 of the embodiments show excellent castability, however, the castiblilities becomes fair or bad when the mean grain sizes become 200 μm or more.

Figure 14A:
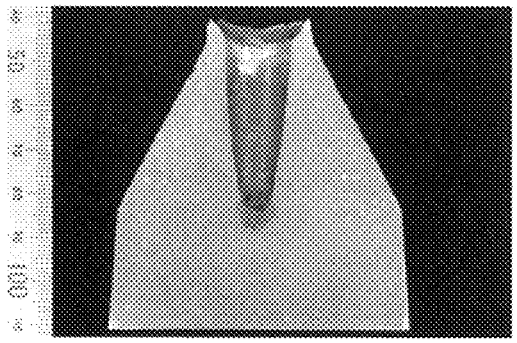
FIGS. 14A to 14C are photographs showing cross-sections of Specimen No. 9 of the embodiments.
Figure 14B:
Figure 14C:
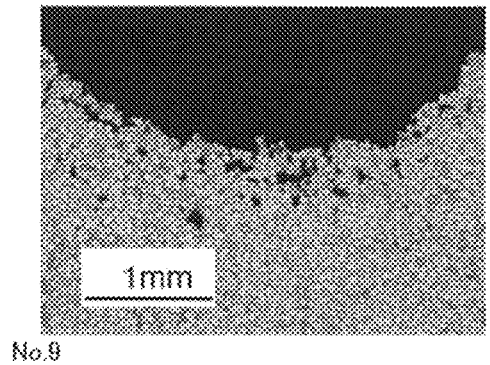
Figure 15A:
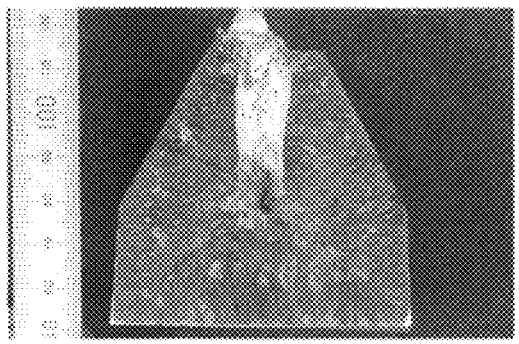
FIGS. 15A to 15C are photographs showing cross-sections of Specimen No. 109 of the comparative example.
Figure 15B:
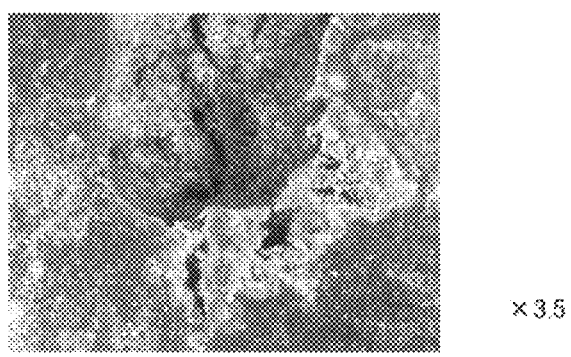
Figure 15C:
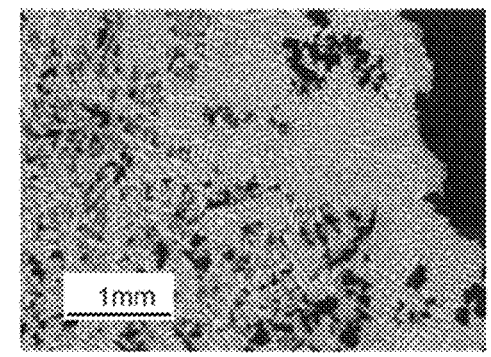

Meanwhile, FIGS. 14 and 15 illustrate the results of Specimens No. 9 and 109. It is evident from the comparison between FIGS. 14B and 14C and FIGS. 15B and 15C that casting defects cannot be discovered in Specimen No. 9 in which the grains are refined, on the contrary, in Specimen No. 109, cracks, cavities and lots of holes are discovered among the arms of dendrites, shrinkage cavities are large, unevenness at the final solidification portion is severe, and casting defects are included.

Next, in order to evaluate the characteristics of the copper-based alloy castings of the invention in which the grains are refined, mechanical properties (tensile strength, proof stress, elongation and fatigue strength) are measured for Specimens No. 8, 9, 12, 29, 39, 44, 122, 110, 111 and 112.

In Specimens No. 110, 111 and 112, the specimens are further heated up to 750° C. and hot-extruded on the condition of the extrusion ratio of 9 and the rolling reduction of 89% so as to fabricate round bars with diameters of 13.3 mm, and then the mean grain sizes and mechanical properties are measured. Meanwhile, hot-extruded specimens are indicated with Specimens No. 110a, 111a, and 112a.

As a mechanical property test, Specimen No. 10 regulated by JIS Z 2201 is adopted among specimens, and tensile test is performed with an Amsler universal testing machine in order to measure the tensile strength, proof stress (0.2%), elongation and fatigue strength. Table 5 illustrates the result.

TABLE 5

| Specimen No. | Mean grain size (μm) | Tensile strength (N/mm$^2$) | 0.2% proof stress (N/mm$^2$) | Elongation (%) | Fatigue strength (N/mm$^2$) |
| --- | --- | --- | --- | --- | --- |
| 8 | 25 (after melt-solidification) | 516 | 257 | 42 | 255 |
| 9 | 15 (after melt-solidification) | 526 | 274 | 42 | 261 |
| 12 | 25 (after melt-solidification) | 520 | 263 | 40 | 257 |
| 29 | 25 (after melt-solidification) | 652 | 345 | 24 | 330 |
| 39 | 20 (after melt-solidification) | 525 | 271 | 30 | 252 |
| 44 | 30 (after melt-solidification) | 605 | 310 | 26 | 285 |
| 122 | 1500 (after melt-solidification) | 388 | 184 | 15 | 159 |
| 110 | 500 (after melt-solidification) | 436 | 181 | 26 | 169 |
| 110a | 30 (after hot working) | 500 | 254 | 37 | 250 |
| 111 | 600 (after melt-solidification) | 433 | 174 | 24 | 155 |
| 111a | 30 (after hot working) | 498 | 251 | 36 | 248 |
| 112 | 150 (after melt-solidification) | 452 | 199 | 30 | 186 |
| 112a | 20 (after hot working) | 524 | 272 | 36 | 258 |

Referring to Table 5, Specimens No. 8, 9, 12, 29, 39 and 44 of the embodiments have better mechanical properties than Specimens No. 122, 110, 111 and 112 of the comparative examples. In addition, since containing Al and Mn, Specimens No. 22 and 44 have better mechanical properties than the other specimens of the embodiments.

It can be found out from the comparison between Specimen No. 39 containing 0.6% of Sn, a low-melting point metal, and Specimen No. 122 that mechanical properties such as strength and elongation, in particular, are considerably improved by the grain refinement, which is attributed to the addition of Zr and P.

In Specimens No. 110 to 112, the grains are large after melt-solidification, however, the grains can be refined as small as 30 μm or less by hot extrusion. Also, mechanical properties of the specimens in which the grains are refined by hot extrusion are almost equal or still inferior to those of the melt-solidified embodiments. It is evident from the above results that the mechanical properties are dependent on the mean grain size. Therefore, it can be found out that the copper-based alloy castings according to the invention, in which the grains are being refined during the melt-solidification, can have the mechanical properties as excellent as those of specimens that are hot-extruded, even though they are not hot-extruded.

The corrosion resistance (erosion•corrosion test, dezincification corrosion test and stress corrosion cracking test) of the specimens shown in Table 6 is examined.

With the erosion•corrosion test, samples taken from the specimens are continuously in contact with a 3% saline solution of 30° C. at a rate of 11 m/s by a 2 mm-diameter nozzle, and then the weight loss due to corrosion is measured after 48 hours. Table 7 illustrates the results.

The dezincification test is based on ISO 6509. Samples taken from the specimens are buried in phenol-resin materials, polished by emery papers up to No. 1200, washed by ultrasonic waves in pure water, and then dried. Samples for the corrosion resistance test obtained by the above procedure are soaked in an aqueous solution (12.7 g/l) of 1.0% cupric chloride dihydrate (CuCl2.2H2O), maintained for 24 hours at 75° C., taken out from the aqueous solution, and then the maximum values of the dezincification corrosion depth (maximum dezincification corrosion depth) are measured. Table 7 illustrates the results.

The stress corrosion cracking test is based on JIS H3250. Tabular samples (10 mm in width, 60 mm in length and 5 mm in depth) taken from the specimens are bent (to add residual tensile stress) at 45 degree so as to have V-shapes (the radius of the bent area is 5 mm), fat-removed, dried, and maintained under the ammonia atmosphere (25° C.) in a desiccator containing 12.5% ammonia water (ammonia diluted with the same amount of pure water). The samples are taken out from the desiccator after predetermined time described below, washed with 10% sulfuric acid, and then the existence of cracks in the samples are observed by a magnifying glass (10 times magnification). Table 6 illustrates the observation results. In Table 6, specimens, in which cracks are not found after 2 hour-maintenance in the ammonia atmosphere, however, found after 8 hour-maintenance, are expressed with 'x', specimens, in which cracks are not found after 8 hour-maintenance, however, found after 24 hour-maintenance, are expressed with 'Δ', and specimens, in which cracks are not found after 24 hour-maintenance, are expressed with 'o'.

TABLE 6

| Specimen No. | Mean grain size (μm) | Weight reduction due to corrosion (mg/cm$^2$) | Maximum corrosion depth (μm) | Stress corrosion cracking resistance |
| --- | --- | --- | --- | --- |
| 8 | 25 | 14.8 | Less than 10 | ○ |
| 9 | 15 | 15.2 | Less than 10 | ○ |
| 15 | 50 | 14.1 | Less than 10 | ○ |
| 42 | 15 | 7.9 | Less than 10 | ○ |
| 33 | 15 | 5.6 | Less than 10 | ○ |
| 103 | 800 | 29.2 | 280 | X |
| 115 | 350 | 18.5 | 180 | Δ |

Referring to Table 6, Specimens No. 8, 9, 15, 42 and 33 of the embodiments in which the grains are refined, have better corrosion resistance than Specimens No. 103 and 115 of the comparative examples. In addition, since containing corrosion resistance-improving elements, Specimens No. 42 and 33 are superior in the weight loss due to corrosion, in particular, to the other specimens of the embodiments.

The outer circumferential surfaces of the specimens shown in Table 7 are cut by a lathe provided with a point nose straight tool (rake angle: −6°, nose R: 0.4 mm) on the condition of the cutting speed of 100 m/minute, the cutting depth of 1.5 mm, the feed of 0.11 mm/rev, power is measured with a three component dynamometer attached to the bite, and calculated into the primary cutting force. Also, the machinability is evaluated from the shapes of chips generated during cutting. That is, when the chips are shaped like fan or circular-arc, that is, half-rotating, the treatability is good, and the specimens are expressed with ⊙. When the chips are shaped like a fine needle, the treatability is good, but there are some dangers in that the debris forms obstacles to machine tools such as lathe or the like, and the debris may be stuck into the operator's finger, whereby the specimens are expressed with '○'. On the other hand, when the debris are shaped like a screw, that is, rotating over three times, there are disadvantages in that cutting treatability deteriorates, debris may be stuck into the bite, and the cutting surface can be damaged, whereby the specimens are expressed with 'x'. Meanwhile, when the debris are shaped like a circular-arc rotating more than half, but, less than one time, or a screw rotating less than three times, even though considerable troubles do not occur, the treatability of the chips deteriorates, the debris may be stuck into the bite during continuous cutting, and then the cutting surfaces are damaged, whereby the specimens are expressed with 'Δ'.

In addition, with the surface roughness, it is ideal that Ry approaches the theoretical surface roughness, and the specimens are expressed with '○' when Ry are less than 7.5 μm. Also, in order to obtain the industrially satisfying cutting surfaces, the specimens are expressed with 'Δ' when Ry are in the range of 7.5 to 12 μm, and the specimens are expressed with 'x' when Ry are more than 12 μm.

TABLE 7

| Specimen No. | Mean grain size | Main cutting force | Shape of chips | Surface state |
|---|---|---|---|---|
| 8 | 25 μm | 118N | ⊙ | ○ |
| 36 | 30 μm | 112N | ⊙ | ○ |
| 39 | 20 μm | 114N | ⊙ | ○ |
| 103 | 800 μm | 161N | X | Δ |
| 107 | 250 μm | 185N | X | Δ |
| 110 | 500 μm | 121N | ⊙ | Δ |
| 113 | 200 μm | 135N | Δ | X |

Referring to Table 7, Specimens No. 8, 36 and 39 of the embodiments in which the grains are refined, have better machinability than Specimens No. 103, 107, 110 and 113 of the comparative examples. Meanwhile, since containing machinability-improving elements, Specimens No. 36 and 39 have smaller primary cutting forces than Specimen No. 8.

The copper-based alloy casting according to the invention, in which the grains are refined during the melt-solidification, can be used as the following structural materials:

Common mechanical parts requiring castability, conductivity, thermal conductivity and high mechanical properties;

Electric terminal and connector requiring high degree of conductivity and thermal conductivity, electric parts, on which alloy brazing and welding can be easily performed;

Gauge parts requiring easy castability;

Metal fittings for water supply and drainage, metal fittings for construction, daily necessities•miscellaneous goods requiring excellent mechanical properties;

Marine propeller, shaft, bearing, valve sheet, valve rod, metal fitting for wrench, cramp, metal fitting for connection, door knob, pipe buckle and cam requiring high strength, hardness and excellent corrosion resistance, toughness;

Valve, stem, bush, worm gear, arm, cylinder parts, valve sheet, stainless bearing and pump impeller requiring high degree of strength, hardness and wear resistance;

Valve, pump chassis, paddle wheel, hydrant, combination tap, water line valve, joint, spring cooler, cock, water meter, water stop valve, sensor parts, scroll type compressor parts, high pressure valve and sleeve pressure vessel requiring pressure resistance, wear resistance, machinability, and castability;

Sliding parts, hydraulic cylinder, cylinder, gear, fishing reel and fastener of airplane requiring excellent hardness and wear resistance Bolt, nut and pipeline connector requiring excellent strength, corrosion resistance and wear resistance;

Chemical machine parts and industrial valve suitable for large sized casting with simple shape and requiring excellent strength, corrosion resistance and wear resistance;

Welded pipe of fresh water generator or the like, hydrant, heat exchanger pipe, heat exchanger tube sheet, gas pipeline pipe, elbow, marine structural material, welding member and welding material requiring bond strength, build-up spraying, lining, overlay, corrosion resistance and castability;

A valve, hexagon cap nut and header hydrant parts requiring excellent stress resistance, wear resistance and machinability;

Sliding bearing requiring malleability, ductility, fatigue resistance and corrosion resistance, heat exchanger, heat exchanger tube sheet and marine parts requiring corrosion resistance and sea water resistance;

Spindle or structural material requiring excellent machinability, malleability and ductility.

Copper-based alloy castings according to the invention have the above compositions and phase structures, and grains are refined to be about 100 μm or less in the mean grain size after melt-solidification.

Since the grains are being refined during the melt-solidification, the castings can endure shrinkage during solidification, and casting cracks hardly occur. In addition, since holes and porosities, generated during solidification, can be removed easily, robust castings without casting defects such as cavities, shrinkage cavities or the like can be fabricated.

In addition, dendrites, crystallized during solidification, have no arms, different from the typical dendrite structure in a casting, that is, a tree-like shape, and are preferably shaped circular, oval, and polygonal or like a cruciform. Therefore, the fluidity of molten alloy improves, and the molten alloy can reach every corner of a thin-walled and complex-shaped mold.

Since having excellent proof stress and the other mechanical properties, corrosion resistance, machinability or the like, the castings, grains of which are refined, are particularly useful for As-Cast products with complex shapes such as valve, joint, water faucet, metal fitting for water supply and drainage or the like.

What is claimed is:
1. A copper-based alloy casting comprising:
69 to 88% of Cu by mass;
2 to 5% of Si by mass;
0.0005 to 0.04% of Zr by mass;
0.01 to 0.25% of P by mass; and
a remainder including Zn and inevitable impurities, and the copper-based alloy casting satisfying 60≤Cu−3.5×Si 3×P≤71, and having refined casted grains,
wherein the grains as cast are refined during melt-solidification of a casting process, and a mean grain size of the refined casted grains is 100 μm or less, and
wherein α, κ and γ-phases of the copper-based alloy casting occupy more than 80% of phase structure of the copper-based alloy casting;
wherein the casting has a shape determined by a mold;

wherein P/Zr is in the range of 0.8 to 250, Si/Zr is in the range of 80 to 6000, and Si/P is in the range of 12 to 220.

2. The copper-based alloy casting according to claim 1, wherein the refined casted grains include dendrites that are crystallized.

3. The copper-based alloy casting according to claim 1, wherein Zr is in the range of 0.0010 to 0.0095% by mass.

4. A copper-based alloy casting comprising:
69 to 88% of Cu by mass;
2 to 5% of Si by mass;
0.0005 to 0.04% of Zr by mass;
0.01 to 0.25% of P by mass;
at least one element selected from the group consisting of 0.1 to 2.5% of Sn, 0.02 to 0.25% of Sb and 0.02 to 0.25% of As, by mass; and
a remainder including Zn and inevitable impurities, and
the copper-based alloy casting satisfying $60 \leq Cu - 3.5 \times Si - 3 \times P \leq 71$, and having refined casted grains;
wherein the grains as cast are refined during melt-solidification of a casting process, and a mean grain size of the refined casted grains is 100 μm or less;
wherein α, κ and γ-phases of the copper-based alloy casting occupy more than 80% of phase structure of the copper-based alloy casting;
wherein the casting has a shape determined by a mold; and
wherein P/Zr is in the range of 0.8 to 250, Si/Zr is in the range of 80 to 6000, and Si/P is in the range of 12 to 220.

5. A copper-based alloy casting comprising:
69 to 88% of Cu by mass;
2 to 5% of Si by mass;
0.0005 to 0.04% of Zr by mass;
0.01 to 0.25% of P by mass;
at least one element selected from the group consisting of 0.004 to 0.45% of Pb, 0.004 to 0.45% of Bi, 0.03 to 0.45% of Se and 0.01 to 0.45% of Te, by mass; and
a remainder including Zn and inevitable impurities,
the copper-based alloy casting satisfying $60 \leq Cu - 3.5 \times Si - 3 \times P \leq 71$, and having refined casted grains, and
wherein the grains as cast are refined during melt-solidification of a casting process, and a mean grain size of the refined casted grains is 100 μm or less;
wherein α, κ and γ-phases of the copper-based alloy casting occupy more than 80% of phase structure of the copper-based alloy casting;
wherein the casting has a shape determined by a mold; and,
wherein P/Zr is in the range of 0.8 to 250, Si/Zr is in the range of 80 to 6000, and Si/P is in the range of 12 to 220.

6. A copper-based alloy casting comprising:
69 to 88% of Cu by mass;
2 to 5% of Si by mass;
0.0005 to 0.04% of Zr by mass;
0.01 to 0.25% of P by mass; and
a remainder including Zn and inevitable impurities, and
the copper-based alloy casting satisfying $60 \leq Cu - 3.5 \times Si - 3 \times P \leq 71$, and having refined casted grains,
wherein the grains as cast are refined during melt-solidification of a casting process, and a mean grain size of the refined casted grains is 100 μm or less,
wherein α, κ and γ-phases of the copper-based alloy casting occupy more than 80% of phase structure of the copper-based alloy casting,
wherein the refined casted grains include crystallized dendrites having shapes with no arms, and
wherein the casting has a shape determined by a mold.

7. A copper-based alloy casting comprising:
69 to 88% of Cu by mass;
2 to 5% of Si by mass;
0.0005 to 0.04% of Zr by mass;
0.01 to 0.25% of P by mass;
at least one element selected from the group consisting of 0.1 to 2.5% of Sn, 0.02 to 0.25% of Sb and 0.02 to 0.25% of As, by mass; and
a remainder including Zn and inevitable impurities, and
the copper-based alloy casting satisfying $60 \leq Cu - 3.5 \times Si - 3 \times P \leq 71$, and having refined casted grains;
wherein the grains as cast are refined during melt-solidification of a casting process, and a mean grain size of the refined casted grains is 100 μm or less;
wherein α, κ and γ-phases of the copper-based alloy casting occupy more than 80% of phase structure of the copper-based alloy casting;
wherein the casting has a shape determined by a mold; and,
wherein the refined casted grains include dendrites that are crystallized, and the dendrites have shapes with no arms.

* * * * *